(12) United States Patent
Conway et al.

(10) Patent No.: US 6,626,888 B1
(45) Date of Patent: Sep. 30, 2003

(54) METHOD OF SHAPING STRUCTURES WITH AN OVERCOAT LAYER INCLUDING FEMALE URINARY CATHETER

(75) Inventors: Anthony J. Conway, Chatfield, MN (US); Philip J. Conway, Chatfield, MN (US); Richard D. Fryar, Jr., Rochester, MN (US)

(73) Assignee: Rochester Medical Corporation, Stewartville, MN (US)

( * ) Notice: Subject to any disclaimer, the term of this patent is extended or adjusted under 35 U.S.C. 154(b) by 0 days.

(21) Appl. No.: 08/533,911

(22) Filed: Sep. 26, 1995

Related U.S. Application Data

(63) Continuation of application No. 08/413,698, filed on Mar. 30, 1995, which is a division of application No. 08/285,026, filed on Aug. 2, 1994, now Pat. No. 5,670,111, which is a continuation-in-part of application No. 07/827,936, filed on Jan. 29, 1992, now Pat. No. 5,360,402, which is a continuation-in-part of application No. 07/809,281, filed on Dec. 13, 1991, now Pat. No. 5,261,896, which is a continuation-in-part of application No. 07/489,462, filed on Mar. 6, 1990, now abandoned, which is a continuation-in-part of application No. 07/487,422, filed on Mar. 1, 1990, now Pat. No. 5,098,379, which is a continuation-in-part of application No. 07/462,832, filed on Jan. 10, 1990, now Pat. No. 5,137,671.

(51) Int. Cl.[7] ............................................. A61M 31/00
(52) U.S. Cl. ....................................... 604/517; 604/500
(58) Field of Search ................................. 604/514, 500, 604/517, 513, 511, 510, 509, 508, 93.01, 96.01, 264, 270, 523, 528

(56) References Cited

U.S. PATENT DOCUMENTS 1,235,142 A     7/1917   Ichilian
1,643,289 A * 9/1927   Peglay ........................ 604/97

(List continued on next page.)

FOREIGN PATENT DOCUMENTS

| CA | 763930 | 7/1967 |
|---|---|---|
| DE | 352014 | 4/1922 |
| DE | 41-35502 | 2/1993 |

(List continued on next page.)

OTHER PUBLICATIONS

"The Merck Index: Ninth Edition", 1976, Merck and Co., Inc., p. 857.

Bayston, "The Antibacterial Effects of Impreganted Silastic and its Possible Applications in Surgery", *J. Pediatric Surgery*, 12, 55–61 (1977).

Bayston, "Preliminary Studies on the Impregnation of Silastic Elastomers with Antimicrobial Substances", *Devel. Medicine and Child Neurol.*, Suppl. (37): 50–54 (1976).

(List continued on next page.)

*Primary Examiner*—Manuel Mendez
(74) *Attorney, Agent, or Firm*—Merchant & Gould, P.C.

(57) ABSTRACT

A method shaping polymeric structures by coating a support structure with a bond-preventing agent to attain a particular shape and subsequently coating the shaped structure of the bond-preventing agent with a polymeric bonding composition is provided. Such shaped polymeric structures can have one or more cavities which can be fluid-filled or gel-filled. Also provided is a hand-actuating retention female urinary catheter having an inner tube and an outer overcoat layer encircling the tube with an elastomeric collar with a shroud. A cavity containing a fluid is interposed between the tube and the overcoat layer. The cavity includes a balloon portion and a reservoir portion. The shroud encircles the reservoir section to inhibit the ballooning of the reservoir section when the reservoir section is squeezed to force fluid from the reservoir portion to the balloon portion through the sleeve portion of the cavity. The overcoat layer and the collar with a shroud are made of soft resilient material.

2 Claims, 15 Drawing Sheets

U.S. PATENT DOCUMENTS

| | | |
|---|---|---|
| 2,043,630 A | 6/1936 | Raiche |
| 2,228,992 A | 1/1941 | Frey .......................... 264/303 |
| 2,230,226 A | 4/1941 | Auzin |
| 2,248,934 A | 7/1941 | Auzin |
| 2,308,484 A | 1/1943 | Auzin et al. |
| 2,314,262 A | 3/1943 | Winder |
| 2,320,157 A | 5/1943 | Raiche ....................... 128/349 |
| 2,322,858 A | 6/1943 | Limbert et al. |
| 2,330,399 A | 9/1943 | Widner |
| 2,330,400 A | 9/1943 | Winder |
| 2,390,070 A | 12/1945 | Auzin |
| 2,481,488 A | 9/1949 | Auzin |
| 2,610,626 A | 9/1952 | Edwards ..................... 128/231 |
| 2,649,619 A | 8/1953 | Killian .......................... 18/24 |
| 2,690,595 A | 10/1954 | Raiche |
| 2,712,161 A | 7/1955 | Moss |
| 3,044,468 A * | 7/1962 | Birtwell ....................... 604/97 |
| 3,053,257 A * | 9/1962 | Birtwell ....................... 604/97 |
| 3,076,464 A | 2/1963 | Rosenburg .................. 264/303 |
| 3,169,527 A | 2/1965 | Sheridan |
| 3,211,151 A * | 10/1965 | Foderick et al. .............. 604/97 |
| 3,304,353 A | 2/1967 | Harautuneian |
| 3,394,705 A | 7/1968 | Abramson |
| 3,409,016 A | 11/1968 | Foley |
| 3,463,141 A | 8/1969 | Mozolf |
| 3,503,400 A | 3/1970 | Osthagen et al. |
| 3,508,959 A | 4/1970 | Krahnke |
| 3,509,884 A | 5/1970 | Bell .......................... 128/350 |
| 3,539,674 A | 11/1970 | Dereniuk et al. |
| 3,544,668 A | 12/1970 | Dereniuk |
| 3,548,805 A * | 12/1970 | Datsenko et al. ......... 604/97 X |
| 3,556,294 A | 1/1971 | Walck, III et al. |
| 3,566,874 A | 3/1971 | Shepherd et al. |
| 3,593,713 A | 7/1971 | Bogoff et al. |
| 3,598,127 A | 8/1971 | Wepsic |
| 3,606,889 A | 9/1971 | Arblaster |
| 3,642,004 A | 2/1972 | Osthagen et al. |
| 3,683,928 A | 8/1972 | Kuntz |
| 3,695,921 A | 10/1972 | Shepherd et al. |
| 3,699,956 A | 10/1972 | Kitrilakis et al. |
| 3,708,324 A | 1/1973 | Stebleton |
| 3,797,478 A | 3/1974 | Walsh et al. |
| 3,838,728 A | 10/1974 | Voegel ....................... 264/221 |
| 3,841,304 A | 10/1974 | Jones |
| 3,854,483 A | 12/1974 | Powers |
| 3,875,937 A | 4/1975 | Schmitt et al. |
| 3,879,516 A | 4/1975 | Wolvek |
| 3,882,220 A | 5/1975 | Ryder ........................ 264/221 |
| 3,889,685 A | 6/1975 | Miller, Jr. et al. |
| 3,894,540 A | 7/1975 | Bonner, Jr. |
| 3,903,893 A | 9/1975 | Scheer ....................... 128/325 |
| 3,924,634 A | 12/1975 | Taylor et al. |
| 3,926,705 A | 12/1975 | Todd |
| 3,981,299 A | 9/1976 | Murray |
| 4,029,104 A | 6/1977 | Kerber |
| 4,062,363 A | 12/1977 | Bonner et al. |
| 4,133,303 A | 1/1979 | Patel |
| 4,149,539 A | 4/1979 | Cianci |
| 4,196,731 A | 4/1980 | Laurin et al. |
| 4,198,984 A | 4/1980 | Taylor |
| 4,225,371 A | 9/1980 | Taylor et al. ................ 156/152 |
| 4,249,535 A | 2/1981 | Hargest, III |
| 4,265,848 A | 5/1981 | Rüsch |
| 4,266,999 A | 5/1981 | Baier ......................... 427/2.3 |
| 4,269,310 A | 5/1981 | Uson |
| 4,284,459 A | 8/1981 | Patel et al. |
| 4,311,146 A | 1/1982 | Wonder ..................... 427/2.3 |
| 4,311,659 A | 1/1982 | Rey et al. ................... 264/317 |
| 4,318,947 A | 3/1982 | Joung |
| 4,378,796 A | 4/1983 | Milhaud |
| 4,381,008 A | 4/1983 | Thomas et al. |
| 4,381,380 A | 4/1983 | LeVeen et al. |
| 4,395,806 A | 8/1983 | Wonder et al. ................ 29/157 |
| 4,457,299 A | 7/1984 | Cornwell |
| 4,472,226 A | 9/1984 | Redinger et al. |
| 4,479,795 A | 10/1984 | Mustacich et al. |
| 4,515,593 A | 5/1985 | Norton |
| 4,539,234 A | 9/1985 | Sakamoto et al. |
| 4,553,533 A | 11/1985 | Leighton |
| 4,563,184 A | 1/1986 | Korol |
| 4,571,239 A | 2/1986 | Heyman |
| 4,571,240 A | 2/1986 | Samson et al. |
| 4,581,026 A | 4/1986 | Schneider ................... 604/352 |
| 4,581,028 A | 4/1986 | Fox, Jr. et al. |
| 4,582,762 A | 4/1986 | Onohara et al. |
| 4,592,920 A | 6/1986 | Murtfeldt |
| 4,601,713 A | 7/1986 | Fuqua |
| 4,603,152 A | 7/1986 | Laurin et al. |
| 4,612,337 A | 9/1986 | Fox, Jr. et al. |
| 4,622,033 A | 11/1986 | Taniguchi |
| 4,623,329 A | 11/1986 | Drobish et al. |
| 4,627,844 A | 12/1986 | Schmitt |
| 4,634,433 A | 1/1987 | Osborne |
| 4,637,907 A | 1/1987 | Hegel ........................ 264/225 |
| 4,652,259 A | 3/1987 | O'Neil |
| 4,664,657 A | 5/1987 | Williamitis et al. |
| 4,677,143 A | 6/1987 | Laurin et al. |
| 4,686,124 A | 8/1987 | Onohara et al. |
| 4,687,470 A | 8/1987 | Okada |
| 4,692,152 A | 9/1987 | Emde |
| 4,710,169 A | 12/1987 | Christopher |
| 4,710,181 A | 12/1987 | Fuqua |
| 4,731,064 A | 3/1988 | Heyden ...................... 604/352 |
| 4,737,219 A | 4/1988 | Taller et al. |
| 4,739,768 A | 4/1988 | Engelson ................... 128/658 |
| 4,747,845 A | 5/1988 | Korol |
| 4,769,013 A | 9/1988 | Lorenz et al. |
| 4,772,473 A | 9/1988 | Patel et al. |
| 4,775,371 A | 10/1988 | Mueller, Jr. |
| 4,813,935 A | 3/1989 | Haber et al. |
| 4,820,270 A | 4/1989 | Hardcastle et al. ......... 264/167 |
| 4,820,292 A | 4/1989 | Korol et al. |
| 4,838,876 A | 6/1989 | Wong et al. |
| 4,850,969 A | 7/1989 | Jackson |
| 4,861,337 A | 8/1989 | George |
| 4,863,424 A | 9/1989 | Blake, III et al. |
| 4,863,444 A | 9/1989 | Blomer |
| 4,874,373 A | 10/1989 | Luther ....................... 604/164 |
| 4,876,109 A | 10/1989 | Mayer et al. .............. 427/2.28 |
| 4,902,503 A | 2/1990 | Umemura et al. |
| 4,904,260 A | 2/1990 | Ray et al. |
| 4,917,686 A | 4/1990 | Bayston et al. |
| 4,923,450 A | 5/1990 | Maeda et al. |
| 4,925,668 A | 5/1990 | Kahn et al. |
| 4,930,522 A | 6/1990 | Busnel et al. |
| 4,932,938 A | 6/1990 | Goldberg |
| 4,935,260 A | 6/1990 | Shlenker |
| 4,950,256 A | 8/1990 | Luther et al. |
| 4,968,507 A | 11/1990 | Zentner et al. |
| 4,976,703 A | 12/1990 | Franetzki et al. |
| 4,981,471 A | 1/1991 | Quinn et al. |
| 4,994,047 A | 2/1991 | Walker et al. |
| 5,013,306 A | 5/1991 | Solomon et al. |
| 5,013,717 A | 5/1991 | Solomon et al. |
| 5,019,096 A | 5/1991 | Fox, Jr. et al. |
| 5,019,378 A | 5/1991 | Allen |
| 5,019,601 A | 5/1991 | Allen |
| 5,071,406 A | 12/1991 | Jang ............................ 604/96 |
| 5,078,707 A | 1/1992 | Peter Klug ................. 604/349 |
| 5,082,006 A | 1/1992 | Jonasson |
| 5,089,205 A | 2/1992 | Huang et al. |

| | | |
|---|---|---|
| 5,090,424 A | 2/1992 | Simon et al. |
| 5,098,379 A | 3/1992 | Conway et al. |
| 5,112,306 A | 5/1992 | Burton et al. |
| 5,128,088 A | 7/1992 | Shimomura ................. 427/273 |
| 5,131,906 A | 7/1992 | Chen |
| 5,137,671 A | 8/1992 | Conway et al. |
| 5,165,952 A | 11/1992 | Solomon et al. ................ 427/2 |
| 5,176,666 A | 1/1993 | Conway et al. .............. 427/2.3 |
| 5,261,896 A | 11/1993 | Conway et al. |
| 5,269,770 A | 12/1993 | Conway et al. ............. 604/265 |
| 5,290,306 A | 3/1994 | Trotta et al. ................. 606/194 |
| 5,306,226 A | 4/1994 | Salama |
| 5,360,402 A | 11/1994 | Conway et al. |
| 5,370,899 A | 12/1994 | Conway et al. .............. 427/2.3 |
| 5,395,333 A | 3/1995 | Brill ........................... 604/101 |
| 5,415,635 A | 5/1995 | Bagaoisan et al. ............ 604/96 |

FOREIGN PATENT DOCUMENTS

| | | |
|---|---|---|
| EP | 0055023 | 6/1982 |
| EP | 0 184 629 | 6/1986 |
| EP | 0 303 487 | 2/1989 |
| FR | 2351634 | 12/1977 |
| GB | 2150938 | 7/1985 |
| GB | 2187670 | 9/1987 |
| JP | 0218157 | 12/1984 |
| JP | 0228856 | 12/1984 |
| RU | 278468 | 5/1970 |
| WO | 84/01102 | 3/1984 |
| WO | 89/09626 | 1/1989 |
| WO | 90/04431 | 5/1990 |
| WO | WO 91/10466 | 7/1991 |
| WO | WO 92/08426 | 5/1992 |
| WO | WO 93/14806 | 8/1993 |

OTHER PUBLICATIONS

Butler et al., "Evaluation of Polymyxin Catheter Lubricant and Impregnated Catheters", *J. Urology*, 100, 560–566 (1968).

S. M. Lazarus et al., "A Hydrophilic Polymer–Coated Antimicrobial Urethral Catheter", *J. Biomed Mater. Res.*, 5, 129–138 (1971).

J. C. Brocklehurst et al., "The Management of Indwelling Catheters", *Brit. J. Urology*, 50(2): 102–105 (1978).

A. M. Johansen and B. Sorensen, "Scand. J. Plast. Reconstr. Surg." 6(1): 47–50 (1972).

K. Miura et al., "The Nitrofurans, in Progress in Medicine Chemistry"; vol. 5 (G.P. Ellis & G.B. West, Eds.); 1967; New York, N.Y.; Plenum; pp. 320–381.

T. Monson et al., "Evaluation of a Polymer–coated Indwelling Catheter in Prevention of Infection", *J. Urology, 111*: 220–222 (1974).

I. Sakamoto et al., "Efficacy of an Antibiotic Coated Indewlling Catheter: A Preliminary Report", *J. Biomed Materials Res. 19*: 1031–1041 (1985).

Z. Shah et al., "Capsular Contracture Around Silicone Implants: The role of Intraluminal Antibiotics", *Plastic and Reconstr. Surg., 69*: 809–814 (1982).

R. Van Noort, "Mechanical Properties of Antibacterial Silicone Rubber for Hydrocephalus Shunts", *J. Biomed. Materials Res.*, 13: 623–630 (1979).

H. Mooro et al., "Prevention of Catheter Fever by the Use of Fruacin Uretheral Inserts", *J. Egypt Med. Assoc. (Egypt)*, 49(8): 550–553 (1966).

J. L. Nosher et al., "Antibiotic bonded Nephrostomy Catheters for Percutaneious Nephrostomies", *Cardiovasc. Interventional Radiol.* 13: 102–106 (1990).

M. Rehula, *Cesk. Farm.* (Czechoslovakia) 39/10: 436–437 (1990).

M. Rehula, *Cesk. Farm.* (Czechoslovakia) 39/8: 349–352 (1990).

D. N. Rushton et al., "Implant Infections and Antibiotic–Impregnated Silicone Rubber Coating", *J. Neurol Neurosurg., Psych.*, 52: 223–229 (1989).

The Bard Hospital Division brochure (copyright on a date unknown pior to Nov. 19, 1989 by C. R. Bard, Inc., Murray Hill, N.J. 07974.

*Kurt K. Nielsen et al., "The Urethral Plug: A New Treatment Modality for Genuine Urinary Stress Incontinence in Women" *The Journal of Urology*, vol. 144, No. 5, Nov. 1990, pps. 1199–1202.

*K. K. Nielsen et al., "The Urethral Plug II: An Alternative Treatment in Women with Genuine Urinary Stress Incontinence", *British Journal of Urology*, (1993) 72, 428–432.

* cited by examiner

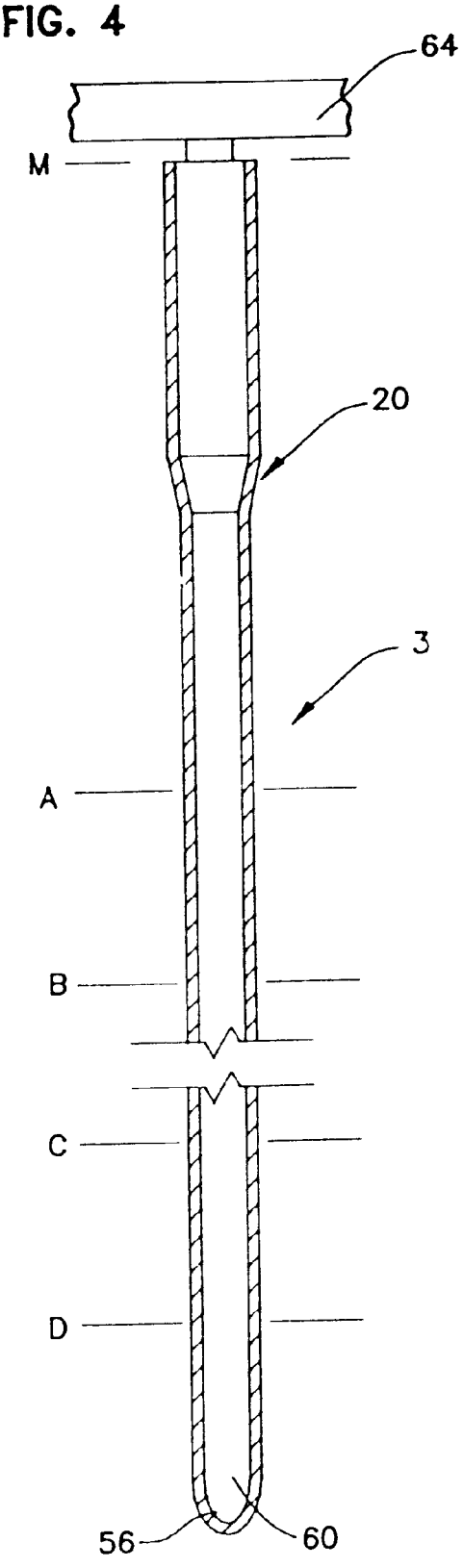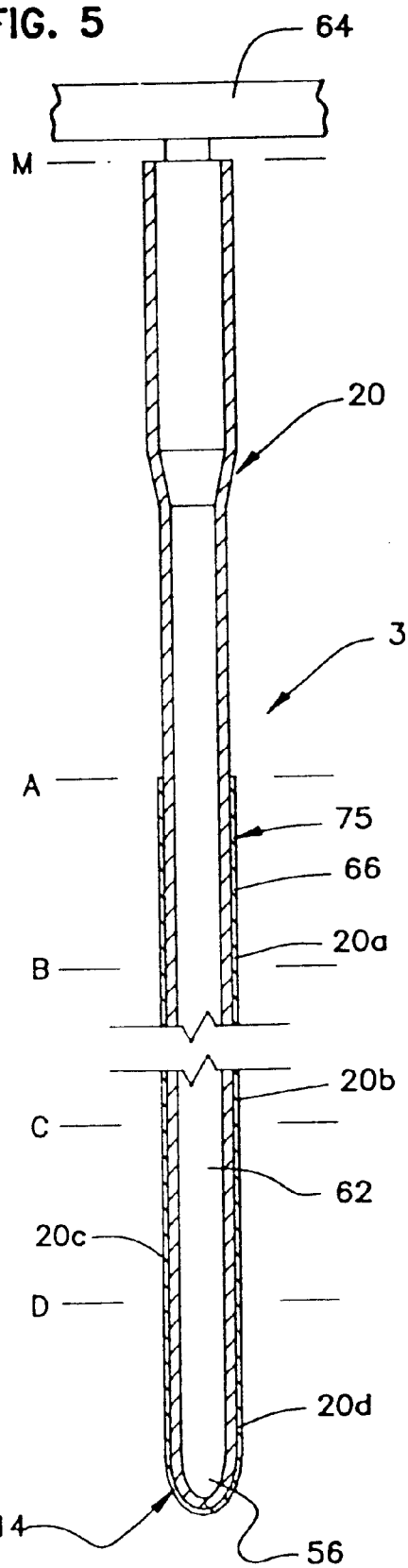

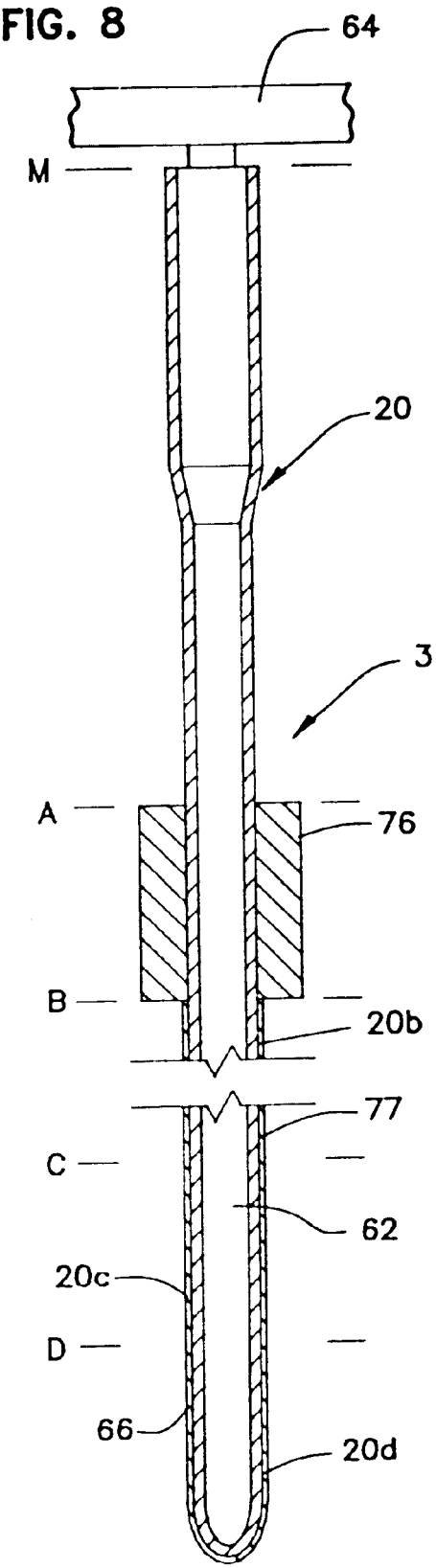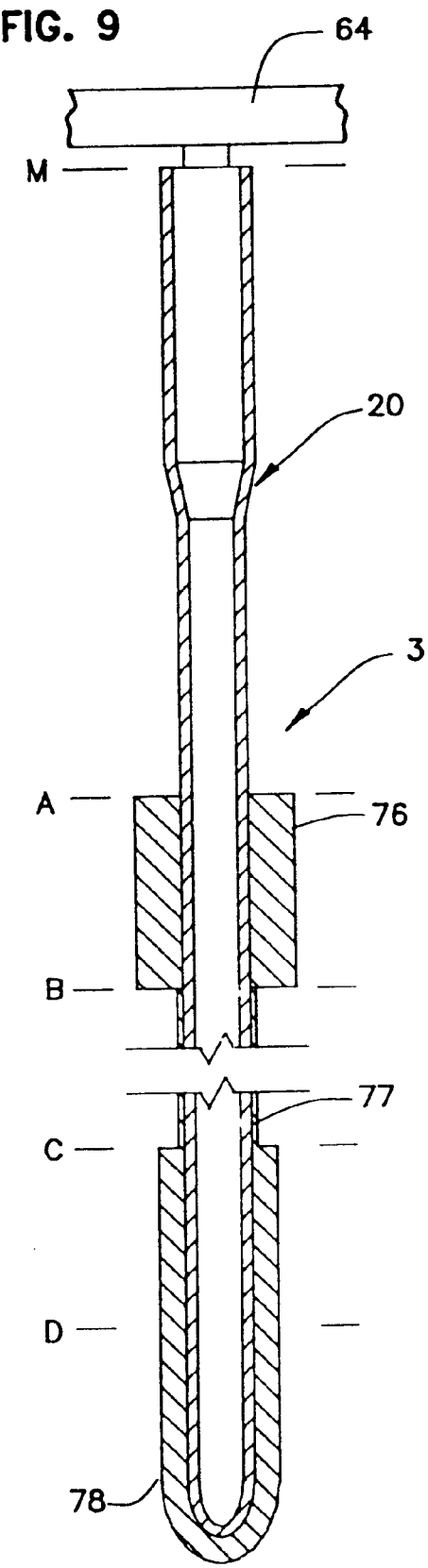

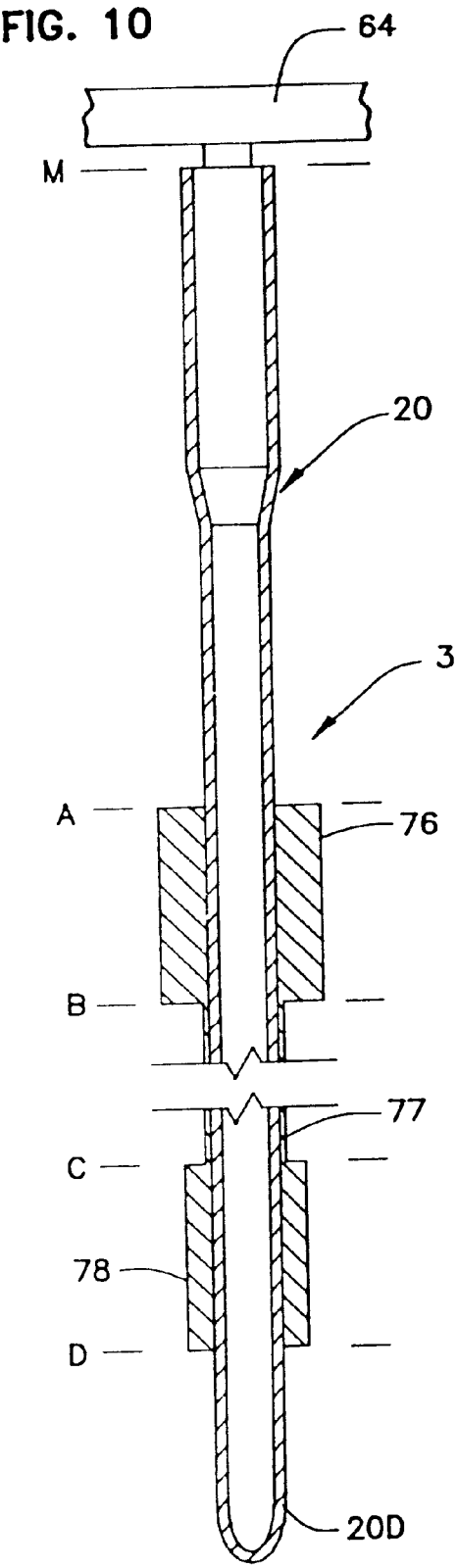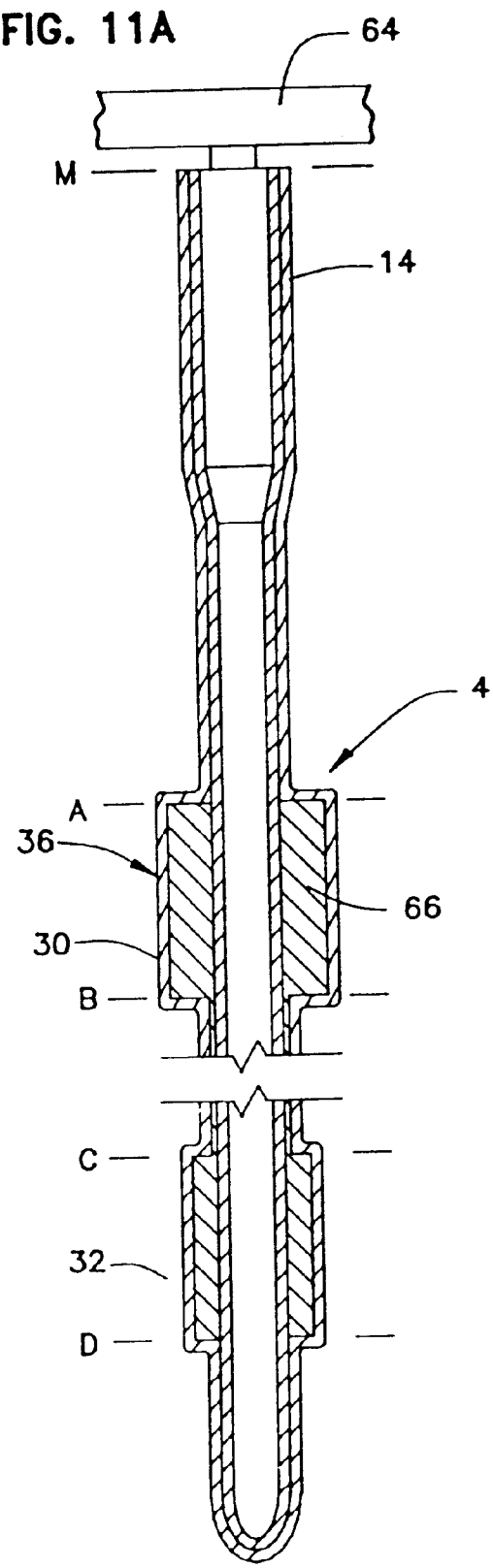

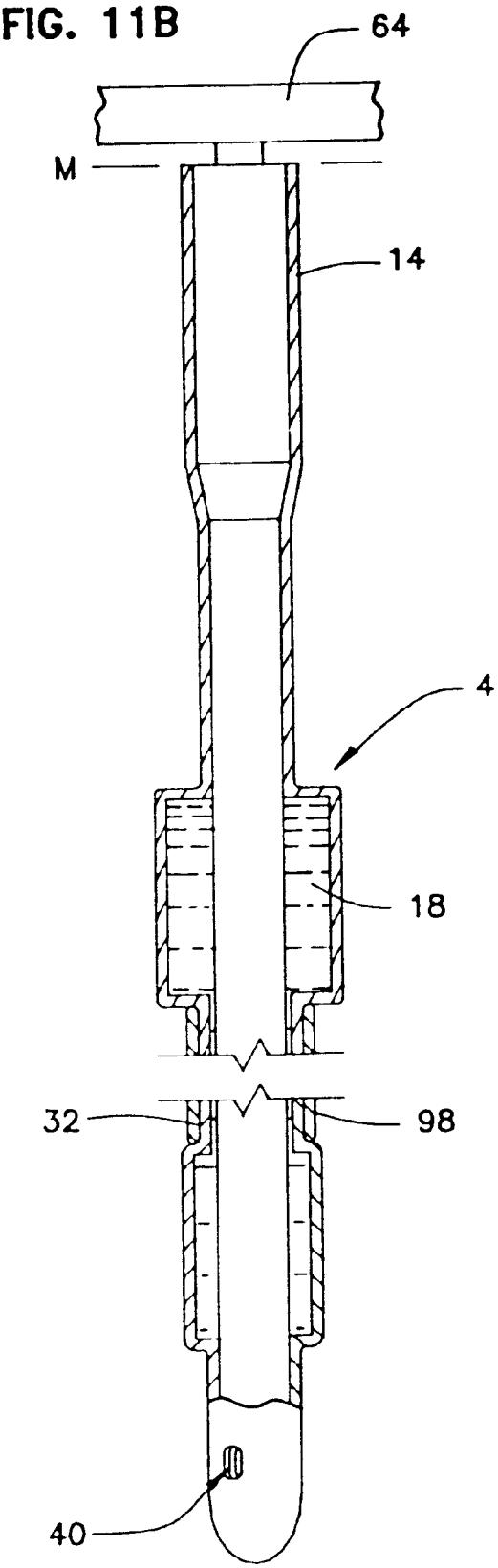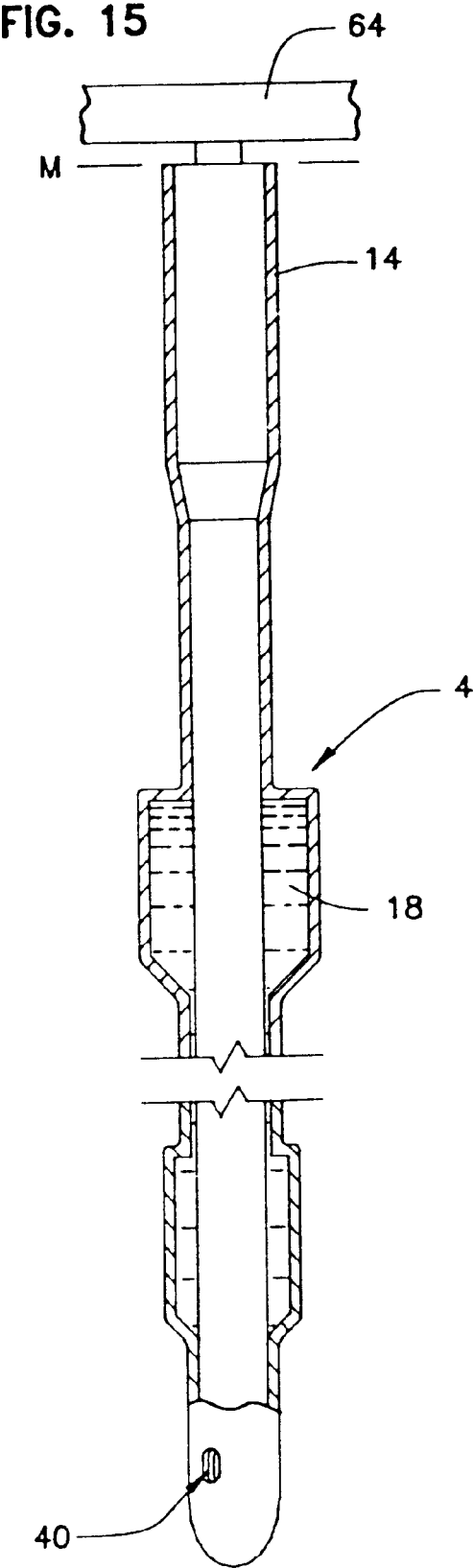

METHOD OF SHAPING STRUCTURES WITH AN OVERCOAT LAYER INCLUDING FEMALE URINARY CATHETER

CROSS-REFERENCE TO OTHER APPLICATIONS

The present application "is a file wrapper continuation of application Ser. No. 08/413,698, filed Mar. 30, 1995, which is a divisional of application Ser. No. 08/285,026, filed Aug. 2, 1994 now U.S. Pat. No. 5,670,111, which" is a continuation-in-part application of U.S. patent application Ser. No. 07/827,936, filed Jan. 29, 1992 now U.S. Pat. No. 5,360,402, which is a continuation-in-part application of U.S. patent application Ser. No. 07/809,281, filed Dec. 13, 1991 now U.S. Pat. No. 5,261,896, which is a continuation-in-part of U.S. patent application Ser. No. 07/489,462, filed Mar. 6, 1990 now abandoned, which is a continuation-in-part application of U.S. patent application Ser. No. 07/487,422, filed Mar. 1, 1990 now U.S. Pat. No. 5,098,379, which is a continuation-in-part application of U.S. patent application Ser. No. 07/462,832, filed Jan. 10, 1990 now U.S. Pat. No. 5,137,671, the disclosures of which are each incorporated herein by reference.

FIELD OF THE INVENTION

The present invention relates to methods of making shaped structures with an overcoat layer. The present invention also relates to making polymeric structures such as cannulas and catheters. In addition, the present invention also relates to urinary catheters and most particularly to female urinary catheters.

BACKGROUND OF THE INVENTION

Many structures, for example, hoses, condoms, gloves, cannulas, catheters, and the like, are made of a polymeric material (e.g., latex, silicone). Such polymeric structures may have various shapes, e.g., sections with different diameters, contours, etc. In addition, various cavities might be present in the structures, some of which might contain fluids of various types. A traditional way to form such structures is by adhesively affixing parts together so that the outer coat can attain the desired shape. However, these traditional methods do not lend themselves to mass production and are labor intensive. Some shapes are extremely difficult if not impossible to make by traditional adhesive methods. likewise, traditional methods of making shaped structures of nonpolymeric substances, such as inorganic materials, with cavities therein sometimes have similar difficulties.

An example of a shaped polymeric structure is a catheter. Most catheters are cannulas or tube like devices which are inserted into a portion of a person's body in order to transport fluids, such as liquids, gases, and sometimes semi-solid material, in or out of that particular portion of the body. For instances, urinary catheters are used to transport urine collected in the bladder out of the body via the urinary tract. Other types of catheters such as gastronomy devices, transport fluids into and out of various segments of the gastrointestinal system, primarily the stomach.

In order to provide a means of retaining the catheter within the body, inflatable bag catheters were introduced many years ago. Subsequently, Foley (U.S. Pat. No. 3,409,016) taught an elongated catheter having a secondary lumen for inflating a retention balloon at a distal end of the catheter once the distal end is positioned within the body. Generally, the "distal end" is the end of the catheter that is first introduced into the body when the catheter is being positioned within the body and the "proximal end" is the end opposite the distal end. Such catheters are now generally referred to as "Foley" catheters out of respect for the contribution made by Dr. Foley. Because of the variation in needs of patients, improvements on Dr. Foley's contribution to the catheter art are continually being made. These improvements sometimes result in cannulas or catheters that have shapes quite different from that of the device originally designed by Dr. Foley.

Traditionally, Foley catheters are made by a process which includes slipping a band of cured rubber over a double lumen latex rubber tubing and affixing the band on the double lumen tubing by dipping the band and the tubing in a suspension of latex to form an outer layer. The cost of manufacturing traditional Foley catheters has been influenced by the need to use a significant amount of hand labor to make the devices, especially the silicone rubber Foley catheters. Moreover, in many cases where a polymeric structure such as a catheter is to have a cavity filled with fluid, traditional manufacturing methods can not be used. It will be appreciated that using such traditional methods to make catheters that have a variety of shapes and sizes of cavities between the tubing and the outer layer would add significantly to the cost of production and pose limitations on the variety of catheters that can be made. Reducing the amount of hand labor in the manufacture of such devices may reduce the cost of such devices so as to provide a more affordable product to the consumer and to render such a product more competitive in the market place.

The same problem of high labor cost and limitation of the variety of shapes is similarly encountered in the manufacture of other shaped structures such as gastronomy devices, condom, and hoses. The present invention provides a method of making polymeric structures which offers substantial advantages over traditional manufacturing methods. In addition, the present invention provides a simple, easily applied, comfortable disposable catheter for incontinent females.

SUMMARY OF THE INVENTION

Method of Making Polymeric Structures

The present invention relates to making a shaped structure by coating at least a portion of a shaped structure of a bond-preventing agent with a liquid composition, e.g. a polymeric bonding composition such as one that contains uncured silicone rubber, to attain an overcoat layer of a desired shape. The shaped structure of a bond-preventing agent can be formed by coating over an outer surface of a support structure, for example, a mandrel or a tube, to form a residual coating of a particular shape.

One embodiment of the present invention relates to dipping a mandrel in a liquid composition, such as polymeric composition to form an inner piece (or structure) over a surface of a mandrel, applying and shaping a residual coating of a bond-preventing agent over the outer surface of the inner piece, and coating at least a portion of the structure resulting from the previous steps with a liquid composition to form a shaped structure having an overcoat on an inner piece.

Another embodiment of the present invention relates to a method of making a polymeric structure in accordance with one of the above methods wherein a fluid-filled cavity is formed between an inner polymeric layer and an outer polymeric layer.

Yet another embodiment of the present invention relates to a method of making a polymeric structure in accordance with one of the above methods wherein an outer polymeric layer only partially encapsulates an inner polymeric layer such that only one end of the outer polymeric layer is attached to the polymeric structure. This method might be utilized to form a polymeric structure having an umbrella-like structure.

It will be appreciated that shaped structures of varying shapes can be formed by the present invention. The shaped structures formed by the present invention might be hollow, liquid-filled, gel-filled, etc. and/or might include a solid piece as well as combinations thereof.

The coating of the bond-preventing agent can have a varying thickness on different portions of an outer surface of the inner piece. The coating of the bond-preventing agent remaining on the inner piece before the coating of the liquid composition is herein referred to as the "residual coating." The shape of the overcoat layer results from the varying thicknesses of the residual coating of the bond-preventing agent.

In one embodiment, the forming of residual coating of varying shapes can be done by coating portions of an outer surface of the inner piece with a bond-preventing agent in a plurality of dipping steps by immersing the inner piece into the bond-preventing agent to a desired depth for a desired length of time and subsequently removing the inner piece from the bond-preventing agent. The desired depth and the desired length of time for each of the plurality of dipping steps is selected so that a residual coating of bond-preventing agent of desired thickness and shape remains on portions of the inner piece following the plurality of dipping steps. The residual coating has a specific shape as a result of the variation between the depth of any two of the plurality of dipping steps, the number of dipping steps, the length of time between any two of the plurality of dipping steps, and the varying speeds of withdrawal from the liquids in dip tanks. By appropriate coating and stripping sequence, the bond-preventing agent can be sculpted to result in desired, symmetrical shapes much as the shapes achievable using a lathe. The sculpted residual coating can have varying thickness, curves, and angles, and therefore a specific, desired shape. By subsequently coating the residual coating of bond-preventing agent, which coats the inner piece, with a polymeric bonding composition, a shaped overcoat layer is formed wherein the shape of the overcoat layer results from the varying shapes of the residual coating. Also, other shaped structures, such as a bullet-shaped, molded, solid polymeric tip can be added to the inner piece before the formation of the overcoat layer to attain a desirable shape for a particular part of the shaped structure with the polymeric overcoat. As used herein, two structures of similar shapes but having unequal ratios of dimensions in the two structures are considered to have different shapes. For example, annular cylinders with the same inside diameter and length but different outside diameters are not considered to have the same shape. As used herein, the residual coating is still considered "a residual coating" even if it is not continuous over two or more portions of the inner piece as long as the coating is not radially separated into layers by a different intervening substance.

In one embodiment, the step of coating the inner piece with the bond-preventing agent can include a step of stripping the inner piece by immersing the inner piece in a stripping fluid to a desired depth for a desired length of time following any of the plurality of dipping steps in order to remove at least a portion of the bond-preventing agent from the outer surface of the inner piece. After the stripping step, the inner piece can be dipped into the bond-preventing agent again to form another coat of the bond-preventing agent on a selected portion of the inner piece if desired. The portion of the inner piece that has been stripped can be dipped in a bond-preventing agent to form a coating. If desired, to form a particular shape, both the stripped portion of the inner piece and a portion of the bond-preventing agent coating that remains on the inner piece can be dipped into the bond-preventing agent. The thickness of the bond-preventing agent coating can be increased by repeating the dipping and removal steps.

In one embodiment the inner piece might be a simple cylindrical mandrel. Such a mandrel can be used for making, for example, a polymeric hose or tube. In another embodiment, the inner piece can be a polymeric tube. Such a polymeric tube can either be purchased or formed by a process that comprises dipping a mandrel in a polymeric bonding composition. Such a polymeric tube typically can have a closed tip at one end.

In an alternate embodiment, a method of mass producing polymeric structures is provided. This method comprises providing a plurality of mandrels, each mandrel having the aforementioned elements; coating portions of an outer surface of the mandrel with a bond-preventing agent in a plurality of dipping steps by immersing the mandrel into the bond-preventing agent to a desired depth for a desired length of time and removing therefrom, stripping portions of the bond-preventing agent by dipping in a stripping agent, and alternately dipping and stripping to achieve the desired shape, and then coating the mandrel, now at least partially coated with the bond-preventing agent, with a polymeric bonding composition to form a shaped overcoat layer.

The present invention enables the production of structures, such as polymeric structures, with a great reduction of hand labor, which not only is costly, but also contribute to inconsistent results. The present invention can be adapted to produce structures of a wide variety of sizes and shapes by varying the thickness of the residual coating of the bond-preventing agent. The variation of the thickness of the residual coating of the bond-preventing agent can be designed to result in a structure with an overcoat of a specific shape. Because of the variation of need for different types of structures, e.g., simple Foley balloon catheters for placement in the urinary tract, balloon catheters with cavities containing bactericidal agents, catheters with cylindrical sleeve with a lubricant, and the like, a variety of shapes are needed for such structures.

The present invention also provides the advantage of obviating the need to machine a solid (such as metallic) mandrel of a specific shape for making a structure with overcoat of that specific shape. Moreover, often such mandrels cannot be used to make overcoat layers of complex shapes. For example, once a polymeric overcoat layer is formed on a mandrel with a shape as that of the inner tube and the coating of bond-preventing agent shown in FIG. 11A, it is very difficult to remove the overcoat layer from the mandrel. Although injection molding using very expensive cavity molds may be used to make structures with overcoat layers, the resulting overcoat layer has "part lines" where the mold is opened to allow removal of the molded structure. Such shortcomings can be overcome by using the method of the present invention.

In the making of polymeric structures using the method of the present invention, the outside dimensions (e.g. diameter) can be made with more consistency than in similar products made by traditional manufacturing methods, such as affixing balloon portions to the outer surface of a tube by hand. The method of the present invention makes possible the highly automated process of fabricating polymeric structures with shaped gel-filled, liquid filled cavities, especially those with a soft, outer, elastomeric layer that can conform to the contour of a surface in contact therewith.

Female Catheter

The present invention further relates to a female catheter having an inner tube and an outer layer encircling the tube. In an embodiment of a female catheter of the present invention, a cavity is interposed between the tube and overcoat layer. A fluid is contained in the cavity. The cavity is enlarged at two spaced apart locations along the inner tube so as to form a balloon portion and a reservoir portion connected by a sleeve section. The sleeve portion is in fluid communication with the balloon and reservoir portions such that fluid is capable of flowing between these portions whereby the size of the balloon and reservoir portions can vary depending on the amount of fluid in each of the portions. The reservoir portion at a proximal end of the catheter is normally in an enlarged state although it is readily compressible into a compressed state. The overcoat has reservoir, sleeve, and balloon sections corresponding to the respective portions of the cavity.

In one embodiment of the invention, a collar encircles the sleeve section of the overcoat to restrict fluid flow between the various portions of the cavity through the sleeve portion and a shroud encircles the reservoir section of the overcoat to limit lateral ballooning thereof when the reservoir section is compressed by forces not completely enveloping the reservoir section.

In another embodiment of the invention, a female catheter as described above further includes a removable stiff plastic stylet inserted into the inner tube to facilitate insertion of the catheter.

The present invention provides a simple, comfortable, disposable female catheter which can be manually inserted by incontinent females and is hand-actuated to achieve retention in a body passageway.

In using one embodiment of the present invention, a distal end of the catheter is inserted into the urethral tract by exerting force on the stylet. Upon emergence into the bladder of the first balloon section at the distal end of the catheter, the fluid in the reservoir portion of the cavity can be forced through the sleeve portion into the balloon portion by compressing the reservoir section of the overcoat layer to inflate the balloon section, thus retaining the catheter in the body passageway. The sleeve section of the catheter can be made to conform to the urethral tract walls providing a leak proof fit. It will be appreciated, that the catheter can allow the inner drain tube to twist and move within the soft outer layer. An elastomeric shroud encircles the reservoir section of the overcoat to limit the lateral ballooning thereof. An elastomeric collar restricts the sleeve section to prevents fluid from being forced back from the balloon portion to the reservoir portion of the cavity during normal activities of the user.

This catheter has the advantage that a limited amount of fluid is confined in the cavity, and therefore the balloon cannot be overinflated. The utilization of a stylet facilitates the insertion of the catheter. The length of the catheter can be designed such that as the reservoir section of the catheter is proximate the outside entrance of the urethra, the balloon section is disposed in the bladder proximate the entrance to the urethra effective to prevent fluid communication between the urethra and the bladder. The catheter can be made with soft material. Because the overcoat layer of the catheter gently conforms to the urethral wall, irritation to the body tissue is greatly reduced, thus lowering the risk of infection. Further, when the catheter is to be withdrawn, the restriction on the sleeve section can be easily removed by pulling the shroud and the collar from the catheter. Therefore, the retention catheter can be easily inserted, positioned, and withdrawn by the patient without the aid of a health professional.

In one embodiment, the fluid in the catheter is mineral oil. The mineral oil migrates to an outer surface of a silicone rubber outer layer to provide a lubricated, low friction surface.

The present invention, its advantages and other objects obtained by its use are also illustrated by the drawings, and the accompanying descriptive material, in which the preferred embodiments of the present invention are described.

BRIEF DESCRIPTION OF THE DRAWINGS

In the drawings, in which like and primed reference numerals indicate corresponding parts throughout the several views.

FIG. 4 is a cross-sectional view of the mandrel shown in FIG. 3 when secured on a moveable pallet, and following the addition of a coating of a polymeric bonding composition to the mandrel;

FIG. 5 is a cross-sectional view similar to that shown in FIG. 4 but after the addition of a coating of a removable bond-preventing agent to a portion of the outer surface of the tube;

FIG. 8 is a transverse schematic view similar to that shown in FIG. 7, but after an additional coating of removable bond-preventing agent has been added to the outer surface of the tube;

FIG. 9 is a transverse schematic view similar to that shown in FIG. 8, but after a further thickness of removable bond-preventing agent is added to the outer surface of the tube;

FIG. 10 is a transverse schematic view similar to that shown in FIG. 9, but after a portion of the removable bond-preventing agent on the outer surface of the tube is removed;

FIG. 11A is a transverse schematic view similar to that shown in FIG. 10, but showing an overcoat layer on the removable bond-preventing agent in cross-section on the outer surface of the tube;

FIG. 11B is a view similar to FIG. 11A except that the bond-preventing agent has been generally replaced by mineral oil;

FIG. 15 is a transverse schematic view similar to that shown in FIG. 11B, but showing another embodiment with transition portions in the distal ends of balloon section and the reservoir section;

DETAILED DESCRIPTION OF THE PREFERRED EMBODIMENTS

The present method can be used to make many different shaped structures with a shaped overcoat. Various structures, ranging from simple structures, such as hoses, balloons, and the like, to more complex-shaped structures, such as condoms, urinary catheters with many portions of different geometries, and the like, can be made in with the method of the present invention.

In a preferred embodiment, the method of shaping a structure having a polymeric overcoat layer can be accomplished by first shaping a structure of bond-preventing agent and then coating the shaped structure of a bond-preventing agent with a polymeric bonding composition to form a shaped overcoat layer. The shaped structure of a bond-preventing agent can be formed by coating the outer surface of an inner piece, such a mandrel or a tube with a bond-preventing agent to result in a residual coating with a desired shape. The coating of the bond-preventing agent can have a varying thickness on different portions of an outer surface of the inner piece, which results in a particular shape in the shaped structure having a polymeric overcoat. The inner piece, if it has a lumen, is preferably made by a dipping process. Similarly, the residual coating and the overcoat layer are preferably made by respective dipping steps in appropriate liquid materials.

Figure 1:
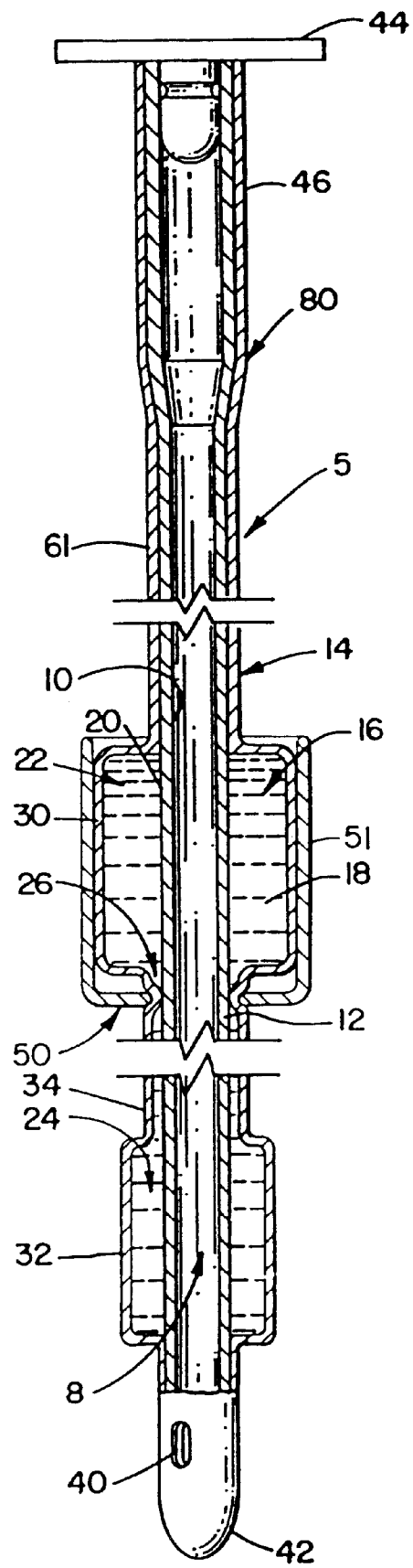
FIG. 1 is a transverse schematic view of a retention catheter made in accordance with the present invention in cross-section.

An embodiment of a female urinary catheter in accordance with of the principle of the present invention is shown in FIG. 1. The catheter can be made with the above method or by other appropriate methods. This catheter 5 has an inner lumen 8 defined by an inner surface 10 of a tube 12. An overcoat layer 14 encircles the tube 12 to define a cavity 16. The cavity 16 contains a fluid 18 and has a fluid reservoir portion (or simply "reservoir portion") 22 and a balloon portion 24 interconnected by a catheter sleeve portion (or simply "sleeve portion") 26 such that fluid 18 can pass between the fluid reservoir portion 22 and the balloon portion 24 via the catheter sleeve portion 26.

Such a catheter is a "hand-actuated retention catheter" and is useful in that a restriction means such as a restriction disc, clamp, elastomeric collar, or elastomeric collar 50 with a shroud 51, can be used to encircle the sleeve portion 26 to restrict fluid from flowing from the balloon portion 24 to the reservoir portion 22 after the balloon portion has been expanded by squeezing the reservoir section of the overcoat (or "squeeze bulb") by hand, thus maintaining the balloon portion 24 in an expanded state to retain the catheter in the desired location in a body passageway. The restriction means is preferably an elastomeric collar 50 with a shroud 51 for limiting the lateral bulging of the squeeze bulb when the squeeze bulb 30 is compressed, for example, between the thumb and the index finger. The restriction means can be loosened or removed to allow fluid to flow from the balloon portion when desired, thus deflating the balloon portion 24 to facilitate removal of the catheter from the body passageway. Preferably, the catheter 5 further includes a stylet for deploying the catheter in the urinary tract.

Method of Making Polymeric Shapes

Figure 2:
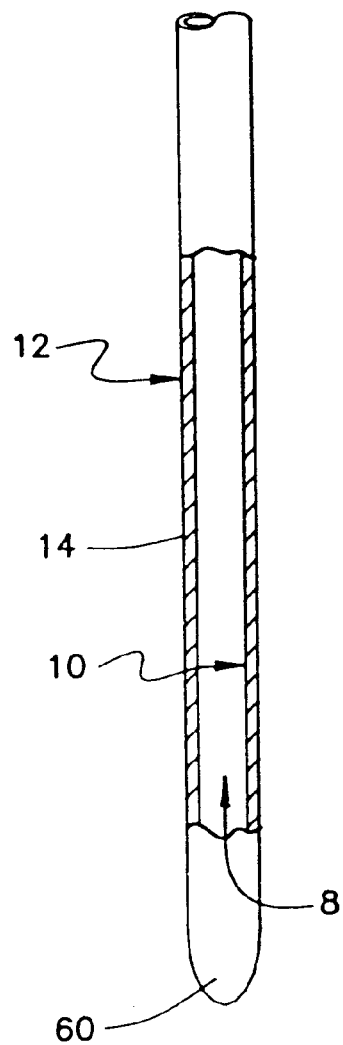
FIG. 2 is a transverse schematic view of a tube in partial cross-section which can be used to make the retention catheter shown in FIG. 1.

To illustrate the application of the present method to forming a shaped, polymeric structure, the embodiment of making a female urinary catheter in accordance of the present invention is described in the following. This embodiment of a female urinary catheter (see FIG. 1) has various portions with different diameters. Referring now to FIG. 2, a resilient, polymeric tube 12 with a closed end, preferably a silicone rubber tube 12, is to be formed first. Although the preferred material for the tube 12 is medically acceptable, silicone rubber, it is to be appreciated that other suitable, medically acceptable polymeric materials may be used. A silicone rubber tube can be made by dipping a mandrel in a polymeric dispersion containing uncured silicone rubber to form a coating and then curing the coating. The uncured silicone rubber for making the tubing is preferably one that will result in a silicone rubber of 50–70 durometer.

Figure 12:
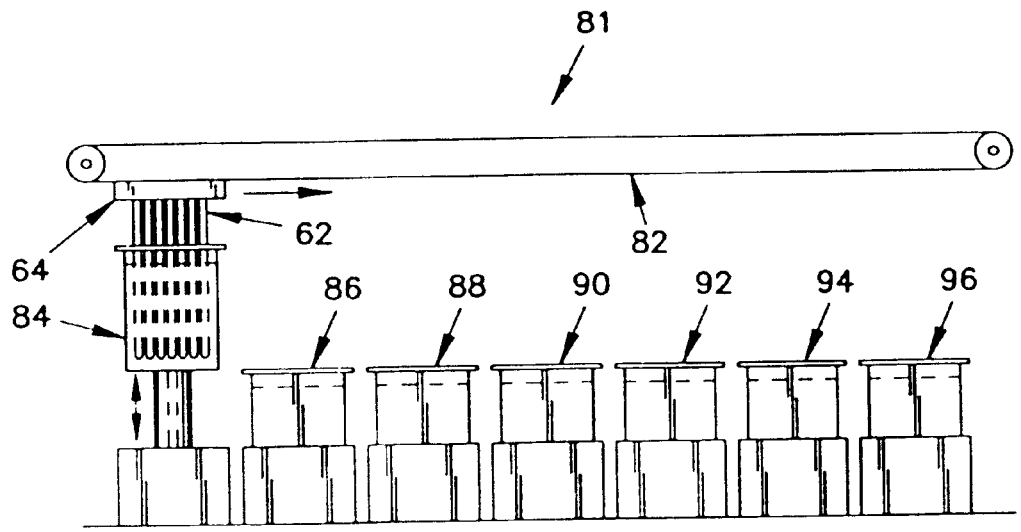
FIG. 12 is a schematic illustration of apparatus used to automate the production of retention catheters in accordance with the present invention similar to that shown in FIG. 1.

Referring now also to FIGS. 3–14, mandrels 62, preferably made of a metal or alloy such as stainless steel or aluminum, are used for forming the catheter of the present invention. The mandrels are preferably coated with a polymer having low surface energy, such as tetrafluroethylene (e.g., TEFLON) so that the completed catheters can be readily removed from the mandrels. FIG. 12 provides a schematic representation of a preferred mechanized catheter production line 81 which is virtually fully automated. FIGS. 13A–C highlights various steps of the automated method which is described below. The mechanized production line 81 includes one or more pallets 64 having a plurality of elongated mandrels 62 each having a generally round or blunt end distal to the pallet. The mandrel 62 preferably has an enlarged section corresponding to a connector portion (or an end piece) 80 proximate the pallet. The end piece 80 can have a transition portion that provides a gradual transition from the wider, proximal end of the end piece to the narrower, inner tubing of the catheter if desired. The moveable pallet 64 is attached to a transport mechanism 82 which can move the pallet to a position over one of a plurality of dip tanks 84,86,88,90,92,94,96. Each of the respective dip tanks will contain a fluid in which mandrels 62 are immersed when the respective dip tank is raised. By dipping in the fluids in these dip tanks, a polymeric tube, shaped residual coating of a bond-preventing agent, and a polymeric overcoat layer are formed on the mandrel to result in a shaped, completed structure.

Figure 14:
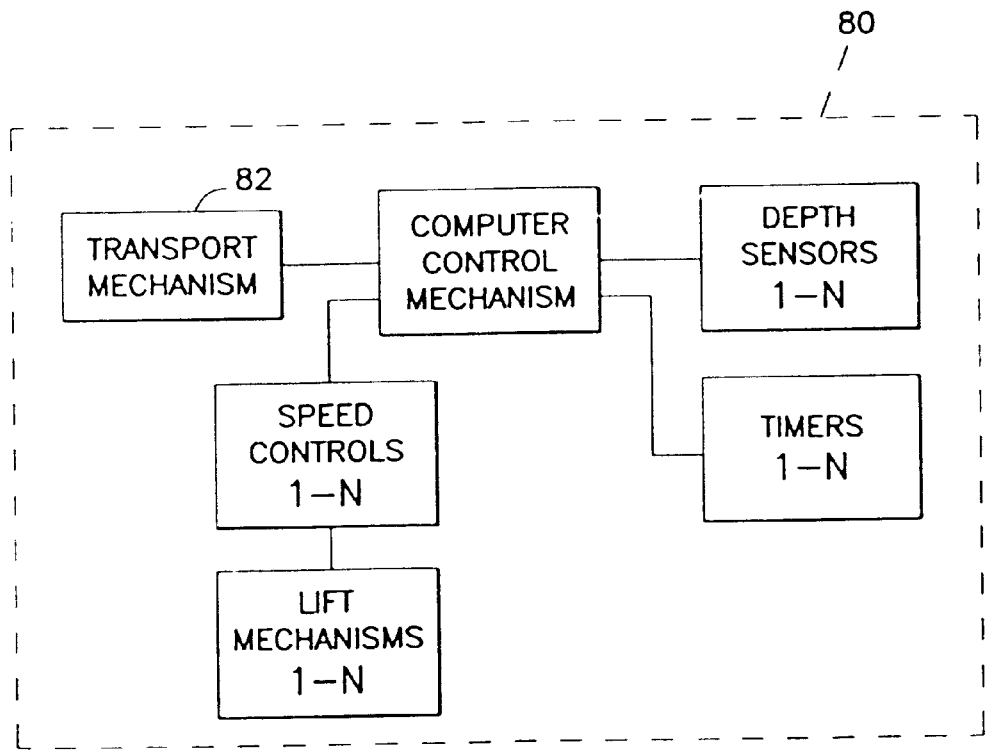
FIG. 14 is a schematic representation of the automated controls for the apparatus shown in FIG. 12, used to automate the production of retention catheters made in accordance with the present invention.

Movement of the pallet 64 is preferably controlled by an output from a computer control mechanism 83, illustrated schematically in FIG. 14, which are directed to the transport mechanism 82. Each of the respective dip tanks 84,86,88, 90,92,94,96 are raised and lowered by associated lift mechanisms. The lift mechanisms are also preferably controlled by outputs from the computer control mechanism 83. Each of the lift mechanisms includes a speed control capable of modulating the rate at which the respective dip tank is raised and lowered so that the speed at which the respective mandrels are immersed into and withdrawn from the respective fluid within the respective dip tank can be varied, either continuously or intermittently, and either during one dipping or between different dippings. The computer control mechanism 83 also receives inputs from depth sensors within each of the respective dip tanks. The depth sensors, preferably ultrasonic depth sensors, are capable of providing an input to the computer control mechanism 83 which enables the computer control mechanism to determine when the mandrels 62 are immersed to a desired depth in the respective dip tank. Timers are also provided for each of the respective dip tanks in order to provide inputs to the computer control mechanism 83 so that the computer control mechanism 83 can determine when a desired period of time has elapsed. A computer program is provided which moves the pallet along the mechanized production line 81 and raises and lowers the respective dip tanks at predetermined times, at predetermined rates of speed, and to predetermined locations and/or heights to enable the mechanized production line 81 to produce a plurality of completed catheters 4 by dipping the mandrels in various dip tanks of fluids. In alternate embodiments, the mechanized production line 81 may have a series of pallets (not shown) which are moved along an alternate transport mechanism (not shown) in series.

After a retention catheter is made, preferably, it is tested. During the testing of the completed retention catheter 5, a removable cylindrical support device 98 is secured around the catheter sleeve section 34 of the overcoat layer 14 interposed between the balloon section 32 and the reservoir as shown in FIG. 11B, to minimize any potential expansion of the catheter sleeve section 34. During testing, the balloon section 32 is expanded and stretched. The step of testing the balloon section 32 helps to create a retention catheter which has a readily expandable balloon section, as opposed to the catheter sleeve section 34 which does not expand as readily upon compression of the fluid reservoir section 30. In addition, the balloon section can be inherently more readily expandable than the sleeve section due to its preferably larger diameter. After testing, the elastomeric collar 50 with a shroud 51 connected thereto is secured onto the catheter 5 by slipping the distal end 42 of the catheter 5 through the collar 50 until the collar encircles the catheter 5 on the catheter sleeve section 34 of the overcoat layer 14 just distal to the squeeze bulb 30 and the shroud encircles the squeeze bulb. In this way, when the squeeze bulb 30 is squeezed by the user, the shroud prevent the squeeze bulb from significantly stretching the portion of the reservoir section of the overcoat not being compressed to cause lateral ballooning (or bulging) thereof.

If desired, the polymeric tube can also be provided by either forming from a suitable tubing (e.g. medically adaptable silicone rubber tubing) purchased or made by an extrusion process known to those skilled in the art. The tubing can be cut to length, have a tip secured thereon, and then be secured to support rods, which can be attached to the pallet. The tip can be affixed to the tube, for example, by using an appropriate adhesive.

In the Applicants' use of the preferred methods of the present invention, production can be almost completely automated. Sets of polymeric structures such as catheters 5 can be manufactured simultaneously. In such preferred automated manufacturing process, the preferred pallet 64 has 400 TEFLON-coated stainless steel mandrels 62 attached to the pallet in 20 rows of 20 mandrels, wherein each of the mandrel 62 is about 1 inch (2.54 cm) from each adjacent mandrel.

Figure 3:
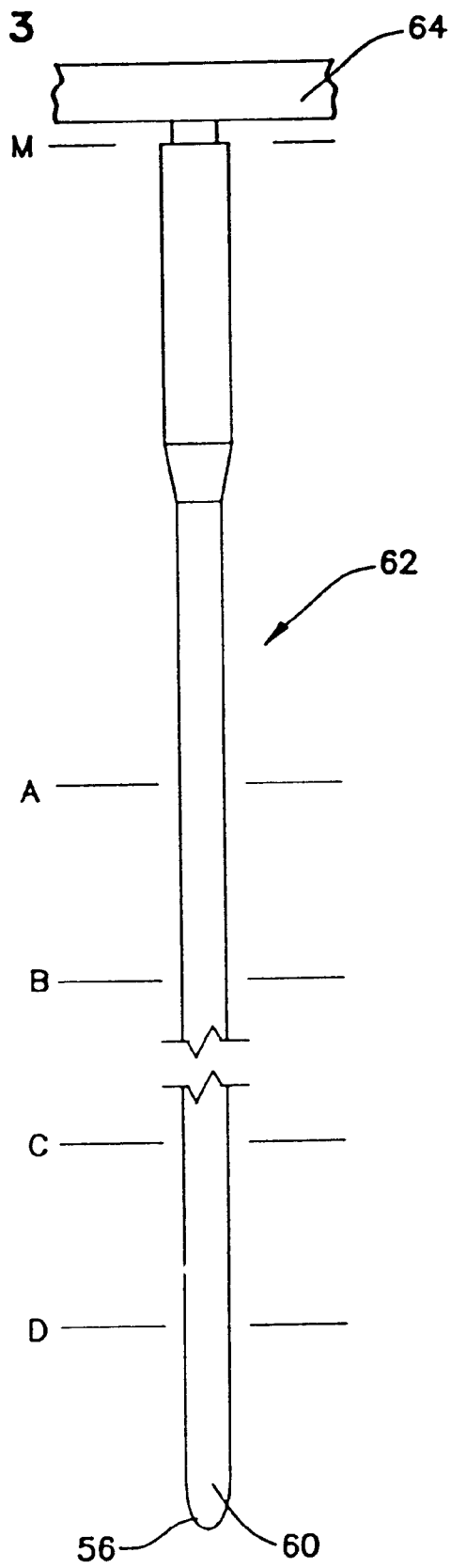
FIG. 3 is a side view of a mandrel for making an embodiment of the retention catheter of the present invention.
Figure 6:
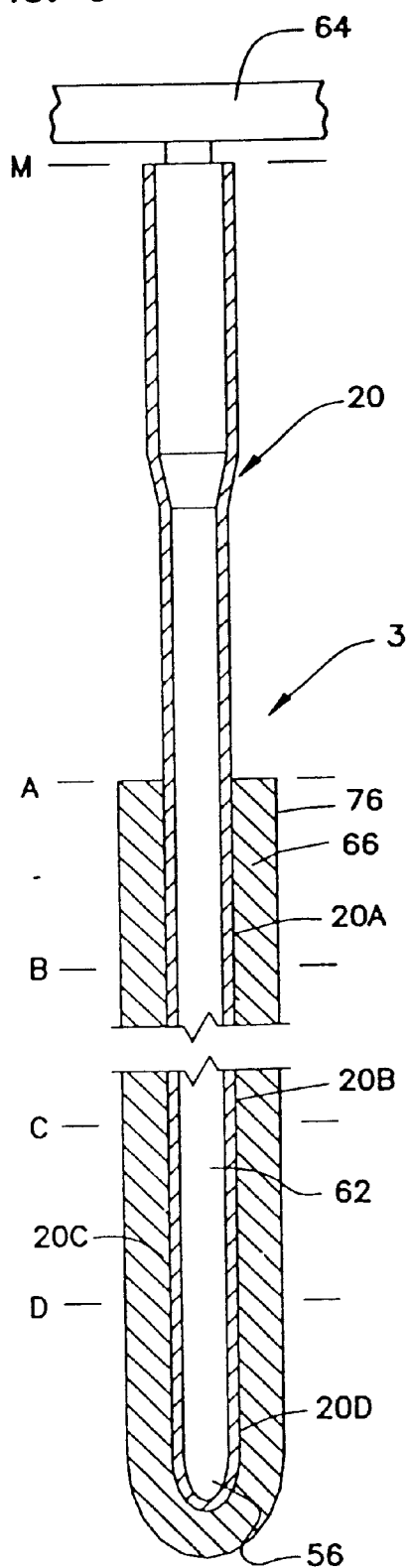
FIG. 6 is a view similar to that shown in FIG. 5, but after the addition of an additional thickness of the removable bond-preventing agent to the outer surface of the tube.
Figure 17:
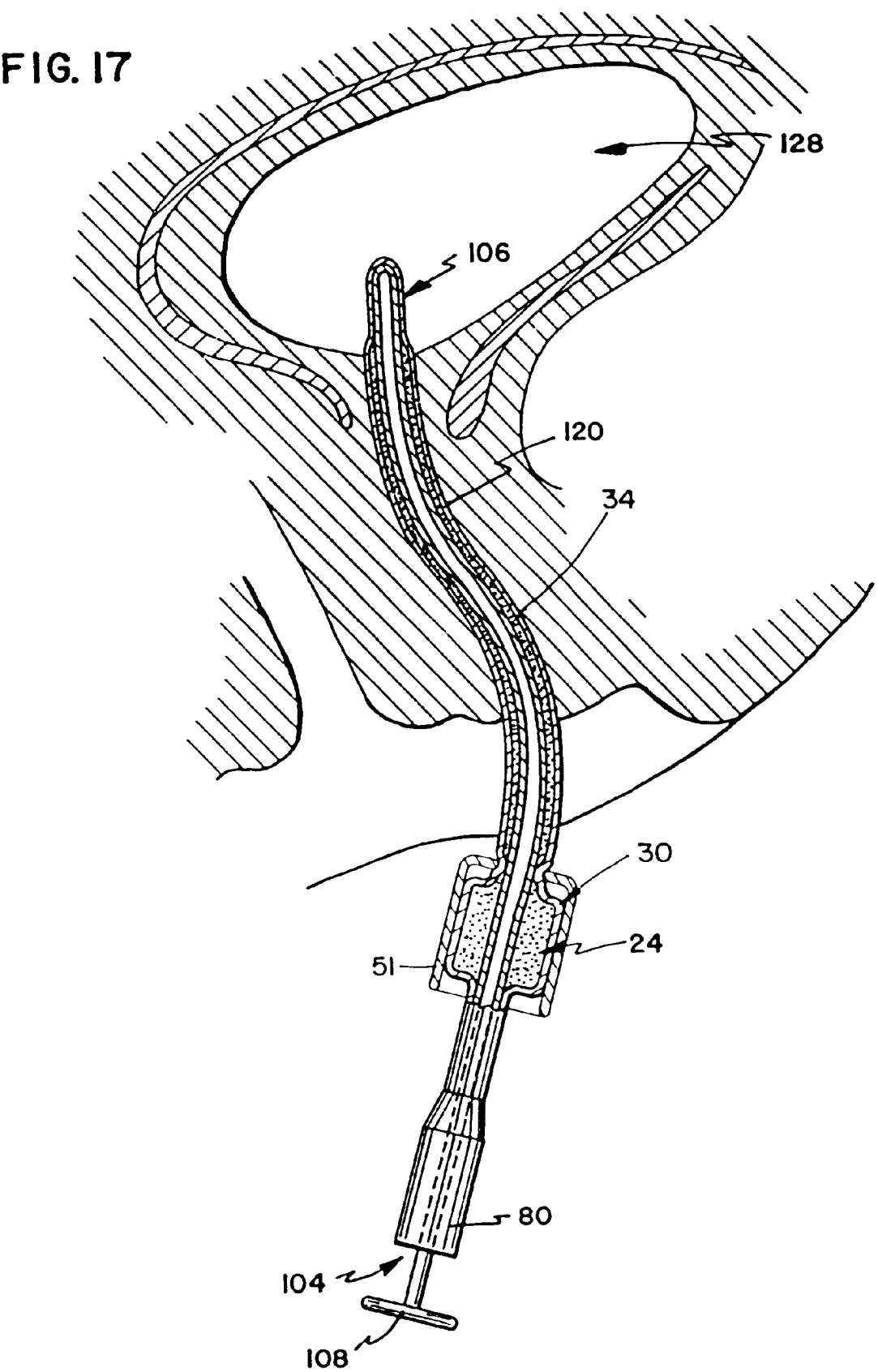
FIG. 17 is a transverse schematic view of showing a cross-section of a catheter of FIG. 1 when being inserted in an urethral tract of a patient, prior to the balloon section emerging into the bladder.

Referring to FIGS. 4–10, in a preferred embodiment of the present method wherein the manufacturing process is automated for mass production of catheters, 400 of TEFLON-coated stainless steel mandrels are mounted vertically on a moveable pallet 64. The pallet 64 is then moved via a transport mechanism 82 (see FIG. 12) over a series of dip tanks 84,86,88,92,94,96 as follows in one of these embodiments:

(A) The pallet 64 is transported to over a first tank 84, which contains a polymeric bonding composition (e.g., an uncured silicone dispersion, for example, a mixture of uncured silicone rubber in toluene that is made by dispersing DOW CORNING Q7-4850 in the solvent (i.e., toluene). The tank 84 is then raised to immerse the mandrels in the uncured silicone dispersion to a depth to cover substantially the whole length of the mandrel such that the uncured silicone rubber dispersion covers the mandrel up to the level of dash line M. The dip tank 84 is then lowered and the outer surface of the mandrel from the distal end up to the dash line M in FIGS. 3–4 is coated with a layer of the uncured silicone rubber dispersion, which is allowed to air-dry for the solvent to evaporate for about 8 minutes. The dipping step is repeated several times to obtain a desirable thickness of uncured silicone rubber coating corresponding to a desired cured silicone rubber thickness. The thickness of the inner tube is preferably about 0.89 mm (0.035 inch), plus or minus 0.1 mm (0.004 inch). The thickness of cured silicone rubber coating on the mandrel is selected such that the completed catheter can be deployed in the body by urging the catheter up the urethra (as shown in FIG. 17 below) with a stylet inserted in the inner tube of the catheter and bearing or biasing against the tip of the inner tube without puncturing the inner tube. When the tank is lowered for the last time, the coating is allowed to air-dry for several minutes, preferably 10 minutes.

(B) The pallet 64 is then advanced to a dip tank (not shown) containing hot USP petrolatum heated to about 210° F. (99° C.) and the uncured silicone rubber coating on the mandrel is cured by dipping in the hot petrolatum for about 0.5 hour and the removed therefrom. Preferably, the cured silicone rubber coating on the mandrel is subsequently dipped in a volatile organic solvent such as toluene to remove all the petrolatum before the next dipping step. Alternatively, the curing can be done by removing the coated mandrels from the transport mechanism and placing them in a hot-air oven (220° F. or 104° C.) for about 0.5 hours to cure the uncured silicone rubber for forming an inner (or intermediate tube). After curing the silicone rubber, the pallet is again secured to the transport mechanism. "An intermediate tube" as used herein refers to a polymeric tube which can be coated with coating of a bond-preventing agent and overcoat layer to form a catheter. Alternatively, the individual mandrels can be placed in the oven separately. Another alternative is to heat the pallet with the mandrels and uncured silicone rubber coating in an oven designed for the whole pallet unit without removing the pallet from the transport mechanism in the production line.

(C) The pallet 64 is then moved and stopped over a second tank 86, which contains a bond-preventing agent 66, such as a petroleum jelly or petrolatum, preferably a liquid petrolatum mixture at about 125° F. (about 52° C.). The mixture will include Perfecta™ Petrolatum USP (from Sonneborn Petrolatums, Sonneborn Div., Witco Chemical Corp., New York, N.Y.). The tank is raised so as to immerse the intermediate tubes 3 into the petrolatum to such a depth (up to dashed line A shown in FIGS. 5 and 6) that the petrolatum coats the first, second, third and fourth portions 20*a*, 20*b*, 20*c* and 20*d* of the outer surface 20 of the intermediate tubes 3. The dip tank 84 is then lowered and these portions of the outer surface 20 are coated with a first coating 75 of petrolatum. The tubes 3 are allowed to air-dry and cool for about 30–60 seconds, and the dip tank is raised again and the tubes 3 are immersed again to the same depth. This is repeated 1015 times until the first coating 75 is built up to a desired thickness (referred to as coating 76 in the drawing, see FIGS. 5 and 6). The desired thickness of the first coating 76 on the tube 3 corresponds to the desired thickness of the reservoir portion 22 of the cavity. Preferably, this thickness is about 1 cm to 2 cm (0.4 in to 0.8 inch) such that the resulting reservoir section of the completed catheter will not be inadvertently drawn into the urethra.

Figure 7:
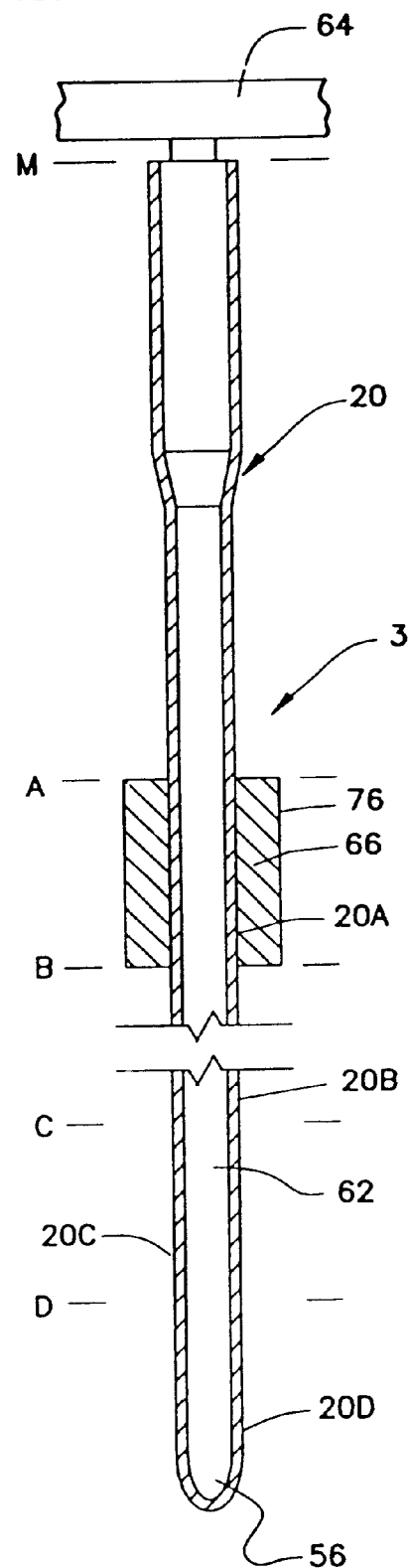
FIG. 7 is a transverse schematic view of the tube shown in FIGS. 4–6, but showing only the removable bond-preventing agent in cross-section and only after a portion thereof has been removed from the outer surface of the tube.

(D) The pallet 64 is then automatically advanced and stopped over a third dip tank 88 which contains hot USP petrolatum heated to about 180° F. (about 82° C.). The third dip tank 88 is raised so as to immerse the intermediate tubes 3 into the super-heated petrolatum for 1 minute so that the super-heated petrolatum comes up to dashed line B-and into contact with the first coating 76 on the second, third and fourth portions 20*b*, 20*c* and 20*d* of the outer surfaces 20 of the intermediate tubes 3 from the prior dipping step. The third dip tank 88 is then lowered. This dipping step causes the coating 76 of petrolatum from the prior dipping step to be largely removed (or stripped) from the second, third and fourth portions 20*b*, 20*c* and 20*d* of the outer surface 20 of the intermediate tubes 3, as shown in FIG. 7. Some residual petrolatum may remain on these portions of the outer surface 20. However, most of the petrolatum is removed from them. The time of dwelling and/or the rate of withdrawal of the mandrels from the stripping fluid can be varied to effect a gradual reduction of the diameter of the distal portion of the first coating 76 remaining on the mandrel, thereby forming a transition portion in the second portion. For example, the time of dwelling of the proximal part of the first coating 76 on the 20*b* portion of the surface 20 in the stripping fluid can be less than the time of dwelling of the more distal part of the same portion to allow more time to strip the distal portion. This can be accomplished, for example, by lowing the dip tank from the dash line B at a decreasing rate for a distance desired for the transition portion.

(E) The pallet 64 is then automatically advanced and stopped over a fourth dip tank 90 containing a liquid petrolatum mixture identical to that in the second dip tank 86, except that the temperature is about 135° F. (about 57° C.). The fourth dip tank 90 is then raised so as to immerse the intermediate tubes 3 into the petrolatum mixture to the same depth as they were immersed in the super-heated petrolatum in the third dip tank 88. In the case where there is a transition portion on the coating remaining on the intermediate tube after the stripping step, the tank is raised to a depth so as to just immerse the distal end of the transition portion. The tank 90 is then lowered, leaving a coating 77 (referred to as the second coating to distinguish from the first coating) of petrolatum on the second, third and fourth portions 20*b*, 20*c* and 20*d* of the outer surface 20, as shown in FIG. 8. If desired, this step can be repeated a few times to build up the thickness of the second coating to have an outside diameter generally corresponding to the diameter of the urethra. The tubes are then immersed again up to the dashed line C and a third coating 78 is created over the third and fourth portions 20*c* and 20*d* of the outer surface 20 (as shown in FIG. 9). Preferably, the dipping step is repeated to build up the the third coating 78 to that it is somewhat thicker than the second coating 77 but thinner than the first coating 76.

(F) The pallet 64 is then automatically advanced and stopped over a fifth dip tank 92 containing hot USP petrolatum like that in the third dip tank 86. The fifth dip tank 92 is raised and the tubes 3 are immersed in the super-heated petrolatum up to the dashed line D for about 30 seconds. The fifth dip tank is then lowered and the third coating 78 of petrolatum is removed from the fourth portion 20*d* of the outer surface 20, as shown in FIG. 10. As before, if desired, a transition portion can be formed by lowering the dip tank 92 gradually or at a decreasing rate once the dip tank has been raised to the desired position. In addition, if desired, part of the residual coatings remaining on the intermediate tube can be further shaped by mechanically removing some of the coatings, for example, by using a knife-like device to sculpture specific shapes thereon.

(G) The pallet 64 is then automatically advanced and stopped over a sixth dip tank 94 containing a volatile organic solvent such as toluene, xylene, or the like, effective to remove all of the bond-preventing agent therefrom so that there will be no interference with the subsequent bonding of silicone rubber to the intermediate tube. The fifth tank 94 is then raised to immerse the intermediate catheters 3 in the organic solvent up to dashed line D (or up to the distal end of the transition portion in the portion 20*d* below the dash line D if a transition portion is present) so as to remove any remaining petrolatum 66 on the fourth portion 20*d* of the outer surface 20. The intermediate catheter tubes 3 now have three bands 76, 77 and 78 of semi-solid petrolatum around the axial circumference of each of the intermediate tubes 3, as shown in FIG. 10.

(H) The tank 64 is then lowered, and the organic solvent is allowed to evaporate from the outer surface 20 for about 15 minutes. The pallet 64 is then automatically advanced to a seventh dip tank 96 containing a hexamethyl disiloxane silicone rubber dispersion which is effective to minimize any disruption of the integrity of the petrolatum coatings 76, 77 and 78 remaining on the intermediate tubes 3. Although the present retention catheter 5 can be constructed of any suitable, medically acceptable, polymeric material, medical grade silicone rubber is preferred. The silicone rubber of the sleeve overcoat preferably is soft, with a hardness of about 20 to 40 durometer, more preferably about 30 durometer. It will be appreciated that such a silicone rubber polymeric must be fully cured prior to sale or use. The overcoat layer can have a thickness of about 0.1 mm to 1 mm, preferably about 0.35 mm plus or minus 0.06 mm (0.0175 inch plus or minus 0.0025 inch). The preferred uncured silicone rubber dispersion is a very soft uncured silicone rubber dissolved in weak solvent that will not attack petroleum jelly. An effective uncured silicone rubber dispersion for making the present invention is a 25–75 mixture of uncured silicone rubber in hexamethyl disiloxane. This mixture is made of GE 603015 LIQUID SILICONE RUBBER and hexamethyl disiloxane. Another example of such an uncured silicone rubber dispersion is Dow Corning Q7-4720 in hexamethyl disiloxane. The seventh dip tank 94 is then raised to immerse essentially the entire length of the intermediate tube 3 in the silicone mixture. This step is preferably subsequently repeated 4–6 times at 8minute intervals to allow time for significant solvent evaporation. When the tank 96 is lowered for the last time, the overcoat layer 14 is allowed to dry and the solvent is allowed to evaporate for about 30 minutes, preferably about an hour. If transition portions are provided on the distal portions of the first coating (in second portion 20b) and the third coating (in fourth portion 20d) as described hereinabove, the resulting completed catheter will have features shown in FIG. 15, which shows a transition portion of a balloon section and a transition portion of a reservoir section.

(I) In a preferred embodiment of the present method, the pallet 24 is advanced to yet another dip tank (not shown) similar to the others, but containing hot USP petrolatum, heated to about 210° F. (about 99° C.). The tubes 3 are completely immersed in the hot petrolatum for 1 hr to cure the uncured silicone rubber and form the completed intermediate catheters 4 shown in FIG. 11A, and the tank (not shown) is then lowered.

(J) The completed intermediate catheters 4 are then removed from the pallets and further cured in hot air at 220° F. (about 104° C.) for about an hour and a half (1.5 hrs).

(K) After the completion of the heat cure, the intermediate catheters 4 are allowed to cool before forming an eyelet 40 each thereon to form the completed retention catheter 5. Preferably, the intermediate catheters are soaked in hot mineral oil at 250° F. (121° C.) for 24–48 hours. The intermediate catheters 4 are then removed from the oil and preferably cleaned.

(L) The completed catheters 5 are finished by punching the fluid conduit access opening or eyelet 40 in the exterior surface 36 of each catheter such that the opening communicates with the fluid conduit lumen 8 in a location below or distal to the balloon section 32. In a device not used for draining fluid, such is a device used for blocking a passageway, for example, for stopping fluid leakage therethrough, such an eyelet may not be needed.

(M) If not previously soaked in mineral oil, the completed catheters 5 are then soaked for preferably 24 to 48 hrs in a hot bath of mineral oil at 250° F. (about 121° C.). The mineral oil will generally replace the petrolatum 66 in the cavity 16 after this period of time, and will remain a fluid 18 at room temperature. The mineral oil has a significantly lower viscosity than petrolatum at room temperature. A different fluid such as water, sterile saline, glycerin, polyethylene glycol, gas (e.g., air) and the like, or appropriate mixtures thereof may also be substituted for the mineral oil/petrolatum fluid in alternate embodiments by removing most of the latter fluid, and then inserting the former by an appropriate means.

(N) The expandable balloon section 32 is then tested and stretched, and then an elastomeric collar 50 with a shroud 51 is put into place over the sleeve section 34 and the reservoir section 30 of the overcoat by slipping over the distal portion of the catheter from the distal end. The completed catheters 5 are packaged and then sterilized prior to shipment.

Figure 13A:
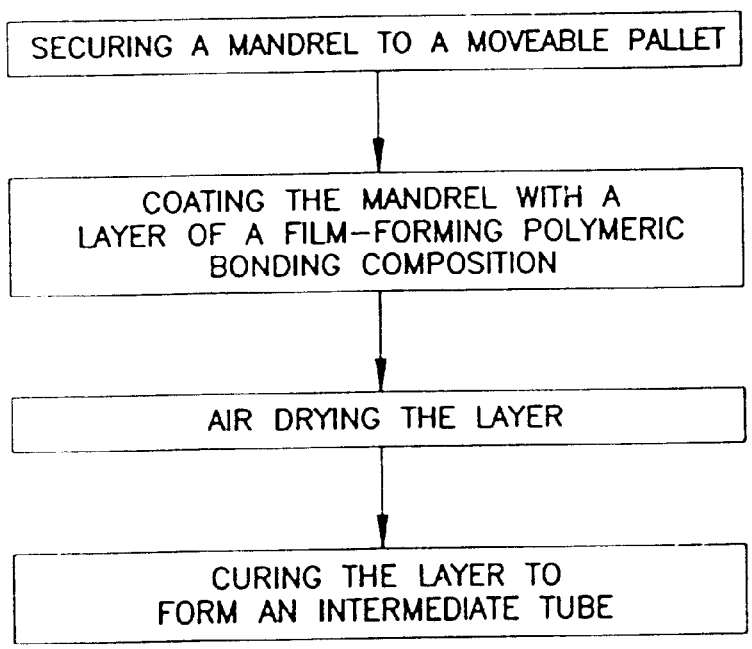
FIGS. 13A, 13B and 13C are flow charts disclosing steps of methods of manufacturing retention catheters in accordance with the present invention.
Figure 13B:
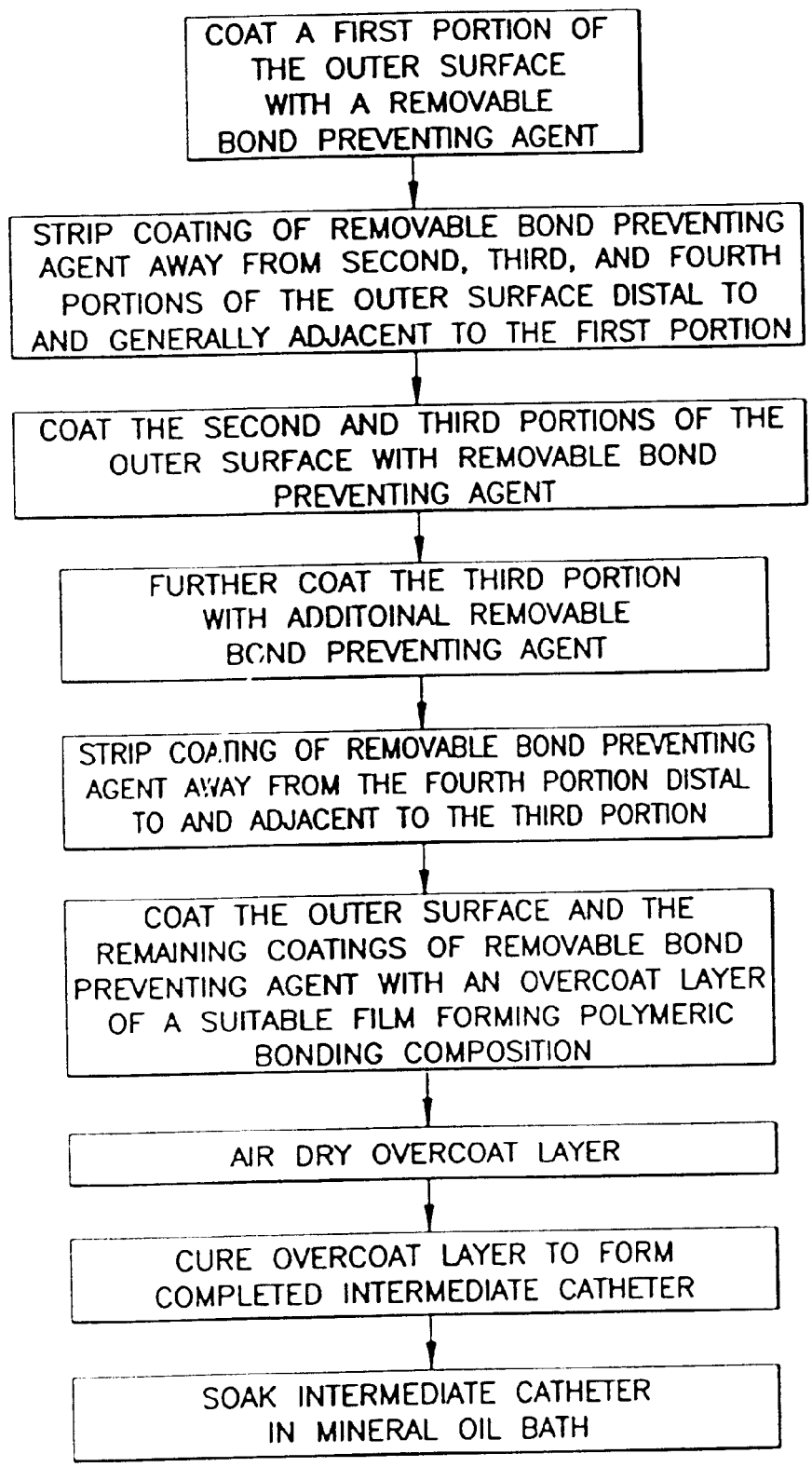
Figure 13C:
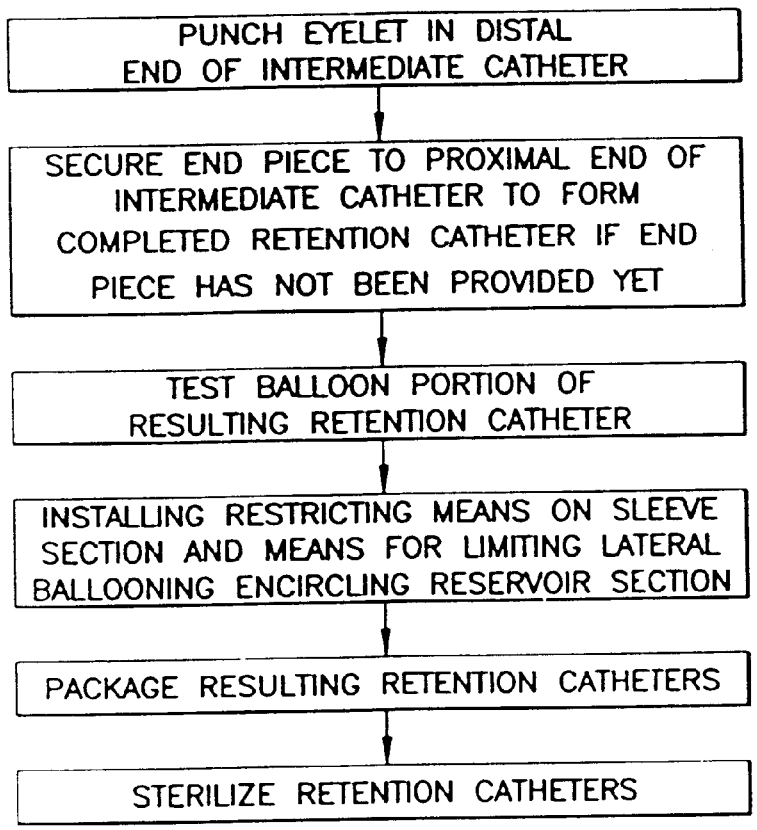

The above process of shaping the preferred embodiment of a hand-actuated catheter is summarized in the flow diagrams in FIGS. 13A, 13B and 13C. The automated method that Applicants claim can permit completed catheters 5 to be manufactured at the rate of about 1,600 catheters per hour. Because little handwork is involved, the catheters 5 produced will be consistent, of very high quality, and less costly to produce than comparable prior art catheters. The exterior surface 36 is believed to be smoother and softer than the exterior surface of hand-glued balloons.

The method of the present invention can be used to make structures having an overcoat layer encircling an inner piece wherein the size of the cavity and the number of cavities can be different from the embodiments described hereinabove. The cavities can be isolated from each other or one or more of the cavities can be connected together to have fluid communication. For example, the cavity defined between an overcoat and the inner tube can have sections with different sizes (such as fluid reservoirs, sleeve cavities, balloons as in the embodiment described hereinabove). Some of the cavities may also be linked by fluid communication means that is not defined between the overcoat layer and the inner tube. These variations affects the shape of the final structure with the overcoat layer, e.g., a catheter. Also, any structure or object, e.g. a conical tip, affixed to the inner piece, e.g., a tube, will also affect the shape of the final structure when the overcoat layer is shaped.

Figure 16:
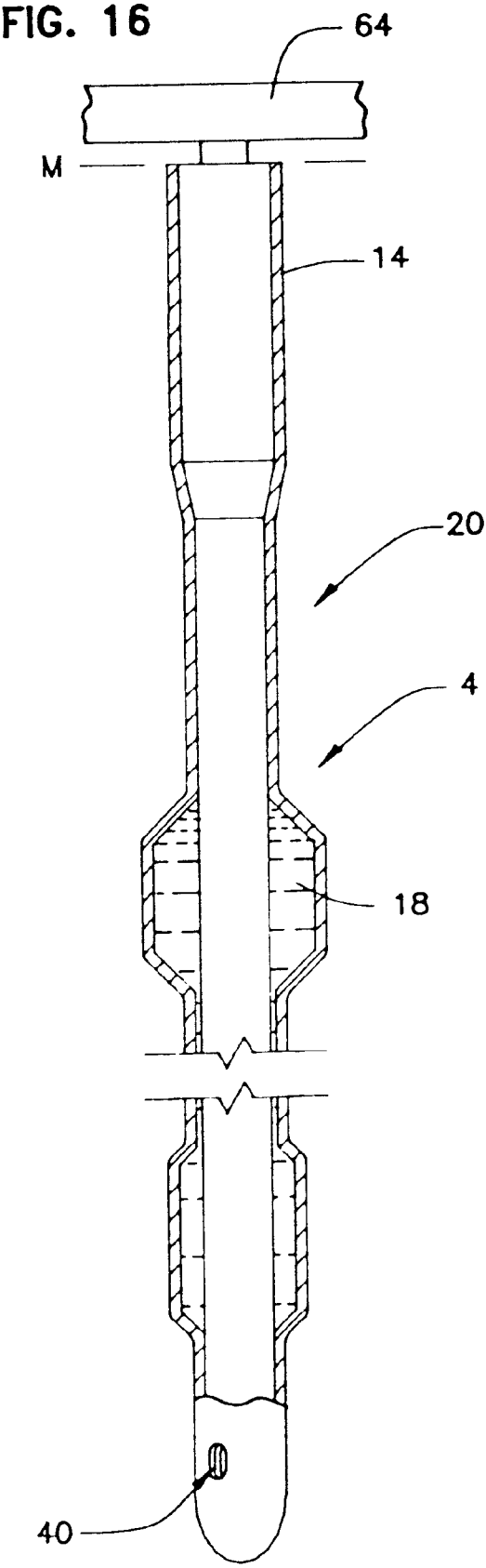
FIG. 16 is a transverse schematic view similar to that shown in FIG. 15, but showing-another embodiment with transition portions in both proximal and distal ends of the balloon section and the reservoir section.

The method can be used to make structures having transition portions on both ends. One embodiment of the process for making a transition portion gradually narrowing distally has been described hereinabove. Transition portions on the proximal ends can be made by immersing the inner piece, e.g., intermediate tube, to a lesser depth in the bond-preventing agent in each succeeding, thickness-building dipping step during the multiple-dipping process in the formation of the residual coating (e.g. the first and the third coating of the bond-preventing agent of FIG. 10). By this method, the proximal ends of the first and third coatings narrow gradually in the proximal direction. By providing such transition portions, structures with various portions of different size can be made to have gradual change rather than abrupt change in shape, for example, a female urinary catheter as shown in FIG. 16.

As previously stated, the present method can be used to make structures that contain a fluid, such as mineral oil. Furthermore, if desired, the completed shaped structure can be a hollow structure, such as a hollow or air-filled balloon. In this case, the inner piece can be pulled from the overcoat layer and the bond-preventing agent or liquid (such as mineral oil) can be squeezed out of the inside cavity of the completed shaped structure. The inner piece can be pulled from the overcoat layer if the inner piece is not in direct contact with the overcoat, as in the case wherein a coating of bond-preventing agent is disposed between the inner piece and the overcoat layer over all the area of the overcoat layer. In another embodiment, the inner piece is coated with a release layer such as TEFLON so that an overcoat layer is not irremovably bonded to it. If desired, the bond-preventing agent can be left in the cavity enclosed by the overcoat layer. As previously stated, the present method can be used to make a simple structure such as a condom. This can be done by a process which includes dipping a mandrel in a bond-preventing for form the shaped structure of bond-preventing agent and coating this structure with a polymeric bonding composition. Depending on the polymeric composition used, a curing step may or may not be necessary. The mandrel and the bond-preventing agent can be removed from the completed condom with appropriate methods.

Figure 21:
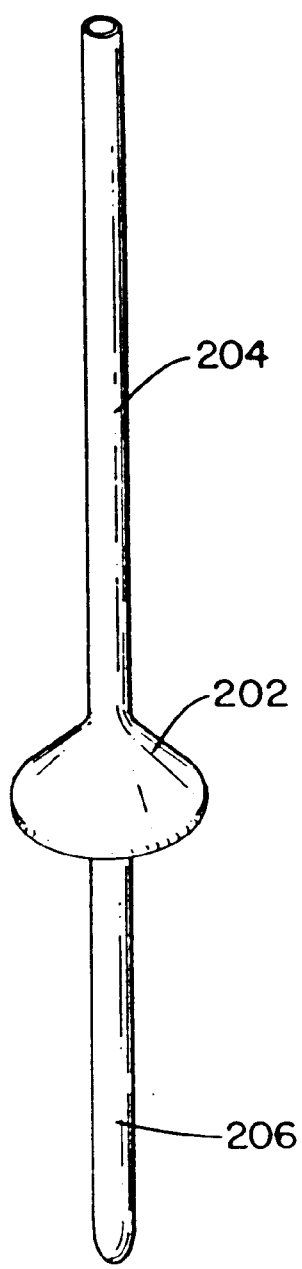
FIG. 21 is an isometric view of another embodiment of a shaped structure made by the method according to the present invention.
Figure 22:
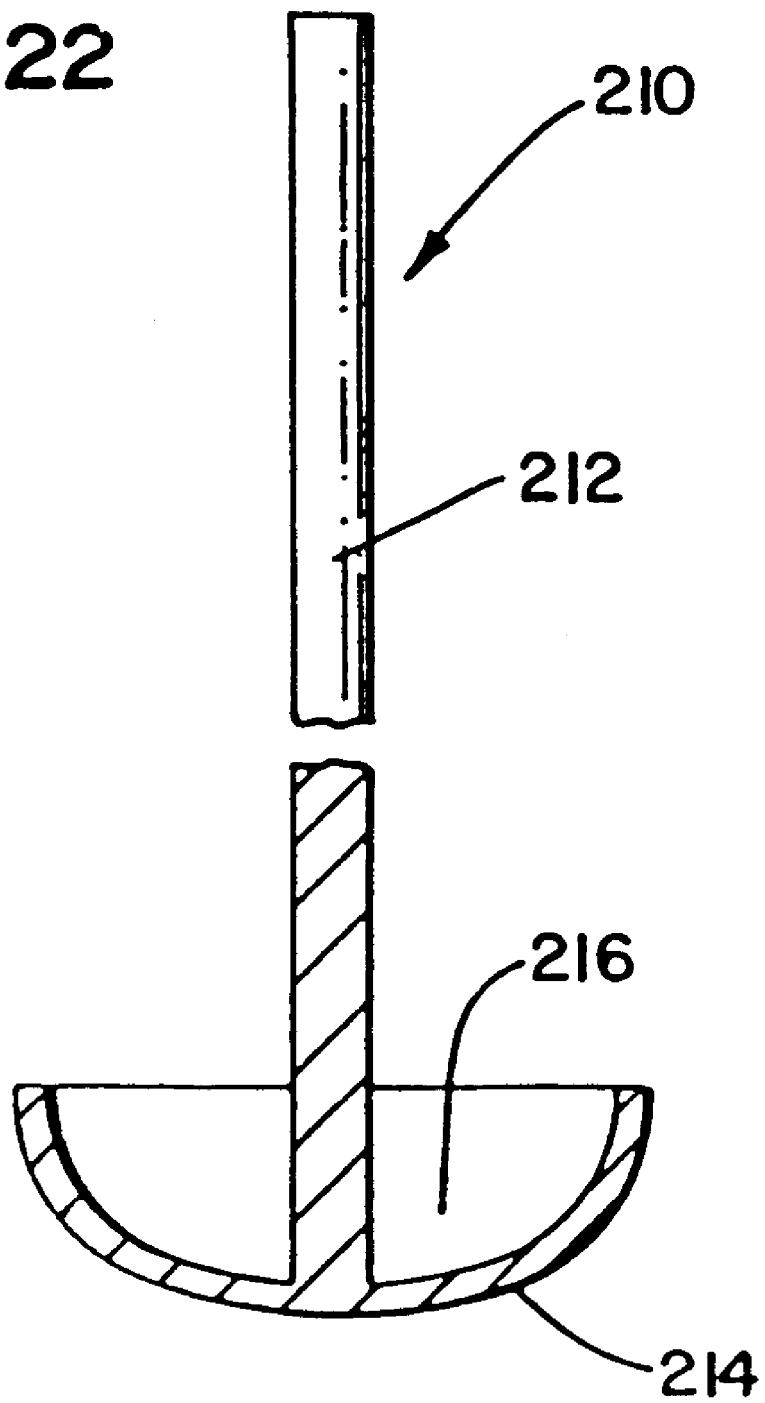
FIG. 22 is a cross-sectional view of yet another embodiment of a shaped structure made by the method according to the present invention.

Therefore, based on the present invention, one can make structures, such as hoses, balloons, condoms, cannulas, catheters, and the like, with one or more sections with different diameters, lengths, or shapes. For example, a hollow structure with a polymeric overcoat of a shape shown in FIG. 21, which has a hollow disc 202 interconnecting and disposed between a first tubular structure 204 and a second tubular structure 206 can be made. Another example is a generally umbrella-shaped polymeric structure as shown in FIG. 22. This generally umbrella-shaped structure 210 has, for example, a cylindrical inner piece (or shaft) 212 (which can be a rod or a tube) and a bowl-shaped outer piece (or hood) 214 integrally connected to an end of the inner piece. The hood encircles the shaft at least partially (e.g., the distal portion or entire length) and defines a recess 216 in cooperation with the shaft at the distal end of the shaft. The periphery of the hood is not attached to the shaft. This structure can be made by a method that includes first forming a cylindrical polymeric inner piece (which can be made by injection molding or by coating a mandrel to form a tube and filling the tube with polymeric material to form a rod), coating the cylindrical inner piece with a residual coating of bond-preventing agent, stripping away the distal portion of the residual coating of bond-preventing agent up to the end of the cylindrical inner piece, and subsequently coating the distal portion of the cylindrical inner piece and the residual coating with a polymeric bonding composition without completely encapsulating or covering the proximal portion of the residual coating. By varying detailed steps of the method, other structures with recesses of various shapes can be formed.

Female Urinary Catheter

The female urinary catheter of the present invention is a hand-actuated retention catheter which is similar to the hand-actuated retention catheter disclosed in U.S. patent application Ser. No. 07/827,936, filed Jan. 29, 1992, the method of making, characteristics, and use of which are incorporated by reference herein. The preferred embodiment (shown in FIG. 1) of the hand-actuated retention catheter 5 of the present invention comprises a tube 12 having outer surface 20 and inner surface 10 and an overcoat layer 14. The tube 12 has an inner lumen 8 which is defined by the inner surface 10 of the tube. The overcoat layer 14 encircles the tube 12 and has interior and exterior surfaces. A cavity 16 is interposed between the tube 12 and the overcoat layer 14. This cavity 16 also encircles the tube 12 and is defined by portions of the outer surface 20 of the tube 12 in cooperation with portions of the interior surface of the overcoat layer 14. This cavity 16 preferably contains a fluid 18, although it can contain a soft, moldable semisolid such as petroleum jelly, or the like, or a combination thereof instead. The overcoat layer 14 includes an expandable, resilient balloon section 32 proximate a distal end, a reservoir (or bulbous) section 30 proximal thereto, and a catheter sleeve section 34 disposed therebetween. The sleeve section 34 interconnects the balloon section 32 and the reservoir section 30. The overcoat layer 14 is joined to the outer surface 20 of the tube 12 at the distal and proximal ends of the cavity 16 (i.e., above and below the cavity) along the tube. The cavity 16 also includes a balloon portion 24, a reservoir portion 22, and a catheter sleeve portion 26 that interconnects the balloon portion and the reservoir portion. The catheter sleeve section 34 of the overcoat layer defines a narrowing in cavity through which fluid passes if made to flow between the balloon portion 24 to the reservoir portion 22. Each of the sections can be cylindrical in shape, or a transition portion that narrows gradually can be provided on one or both ends of the balloon section and/or the reservoir section to facilitate smooth insertion and withdraw of the catheter into the body. The balloon section of the overcoat and the balloon portion of the cavity are of a size such that when the balloon is expanded, it is effective to prevent withdrawal of the balloon section into the urethra in contact with the catheter. Disposed on the sleeve section 34 proximate the squeeze bulb 30 is an elastomeric collar 50 with a shroud 51, which encloses the squeeze bulb. The shroud 51 is preferably, but not necessarily, unitary and integral with the collar 50. The shroud 51 can be connected with the outer edge of the collar 50 such that they resemble a cylindrical cap with an end disc having an opening in the center of the end disc. In another embodiment (not shown), the shroud can be separate from the collar and the shroud can have an ellipsoid shape with open ends which have diameters larger than that of the sleeve section 34 to generally conform to the shape of the reservoir section 30.

The collar 50 presses radially inward on the sleeve so that fluid is prevented from flowing from the balloon portion of to the reservoir portion of the cavity during normal, everyday activities of the user. However, when the catheter is being deployed, the fluid can be deliberately forced past the sleeve section of the cavity by squeezing the squeeze bulb, thus forcing the inside diameter of the collar to slightly increase. In this manner, the balloon section is expanded (i.e. inflated) to retain the catheter in the body passageway.

Preferably, the collar 50 and shroud 51 are made of a material soft and resilient enough such that when desired, they can be readily pulled along the catheter over the reservoir section. Preferably, the shroud 51 is generally cylindrical with an inside diameter of about the outside diameter of the squeeze bulb so that it can be readily slipped over the squeeze bulb 30 during assembly of the catheter. When a force is not being applied from an external source, as by compressing with a thumb and a finger, preferably the shroud does not compress the squeeze bulb. Without the shroud 51, when the squeeze bulb 30 is 43 squeezed to force the fluid from the reservoir portion 22 to the balloon portion 24 through the sleeve portion 26 of the cavity, for example, as when being compress between the thumb and index finger of an user, because of the resistance to fluid flow caused by the restricting collar, the squeeze bulb 30 has a tendency to balloon or bulge out in a direction perpendicular to the direction of the applied compression force, i.e. generally lateral to the axis of the catheter. This is because when compressing forces are not applied in an enveloping manner on the squeeze bulb, the fluid in the squeeze tends to balloon out at the locations with the least compressing force. Such lateral ballooning in the squeeze bulb 30 decreases the efficiency of the squeezing action and make it relatively difficult to expand the balloon portion 24 of the cavity. A shroud 51 encircling the squeeze bulb 30 inhibits he lateral ballooning of the squeeze bulb as it is being squeezed, thus directing the compressing force of the squeezing action to force the fluid to increase the inside diameter of the collar. In this way, fluid is passed to expand the balloon portion 24. The shroud 51 is preferably constructed of a silicone rubber which is soft and pliable and has a thickness making it relatively less stretchable than the overcoat layer on the squeeze bulb 30 and the balloon section 32 so that the shroud can inhibit the lateral ballooning of the squeeze bulb 30 when the squeeze bulb is compressed to force fluid past the sleeve section restricted by the collar 50. The elastomeric collar and shroud can be made with the same silicone rubber material that is used for constructing the inner polymeric tube 12 or the overcoat layer 14. The elastomeric collar and shroud can be made with conventional methods such as injection-molding, or if preferred, with an overcoat-shaping method through dipping in a polymeric material similar to that described above.

Figure 18:
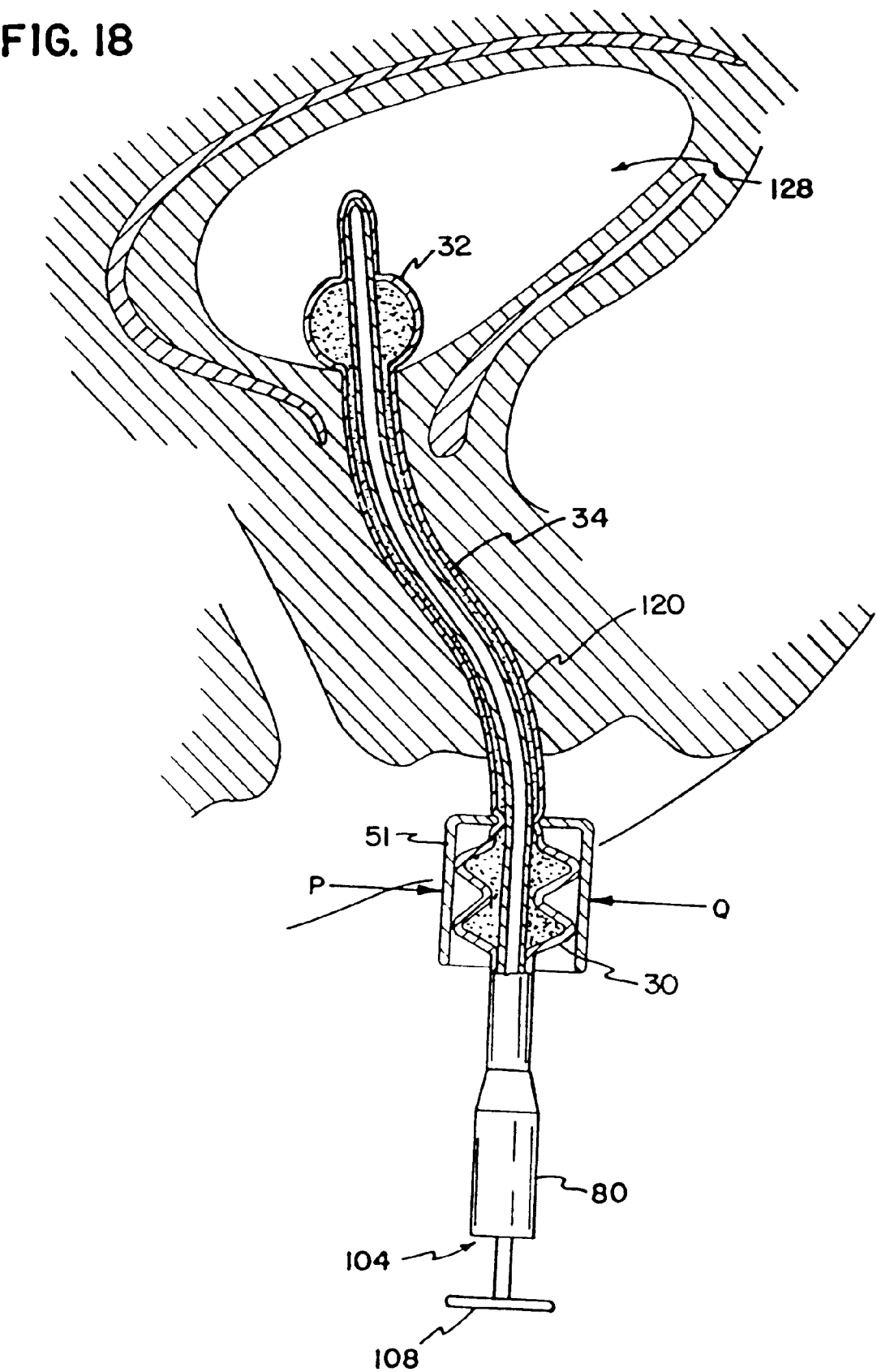
FIG. 18 is a view similar to that shown in FIG. 17, but showing the balloon section of the catheter having emerged into the bladder and is being inflated.

The female urinary catheter described hereinabove can be used in the following fashion. Referring to FIGS. 17–18, first, an elongated, stiff, but slightly flexible stylet 104 is removably inserted into the catheter 5 through the opening at the connector or end piece 80. Such a stylet is preferably made with- plastic and has a diameter slightly smaller than the inside diameter of the inner tube of the catheter for easy insertion and withdrawal. The stylet preferably has a round or blunt distal end 106 and a proximal end having a generally flat end portion 108 generally perpendicular to the elongated part of the stylet. If desired, the flat end portion can extend with its plane parallel to the axis of the stylet. The proximal end portion 108 of the stylet can also be of a shape (e.g., bulb-shaped) for a person's hand to comfortably press thereon to urge the stylet into the catheter and bear against the tip of the catheter. The length of the stylet is slightly longer than the length of the catheter such that when inserted all the way inside a catheter with the distal end of the stylet bearing against the tip of the catheter, the proximal end portion 108 of the stylet 104 is outside and proximal to the end piece 80 of the catheter 5.

The tip of the catheter is then inserted into the urethral tract 120. By generally pressing on the proximal end portion 108 of the stylet, the balloon section of the catheter is slowly urged into the urethral tract. The catheter is slowly advanced into the urethra until the balloon section 32 reaches and emerges into the space inside the bladder 128 and the squeeze bulb (or reservoir section) 30 of the catheter reaches the external opening of the urethra.

Referring to FIG. 18, after the balloon section 32 emerges from the urethra, the squeeze bulb 30, encircled by the shroud 51, is squeezed, for example, between a thumb and an index finger, to force the fluid 18 from the reservoir portion 22 into the balloon portion 24 through the sleeve portion 26. Strong enough forces are applied (the directions of application are shown by the arrows P and Q) to overcome the compression force by the collar 50 so that fluid can pass through the sleeve portion 26 to inflate the balloon section of the overcoat 32. The shroud 51 inhibits any significant ballooning of the squeeze bulb 30 in a direction perpendicular to the applied forces P and Q. The collar 50 prevents fluid that has been previously forced out of the reservoir portion of the cavity from flowing back thereinto, thus maintaining the balloon portion 24 in an expanded state to retain the catheter in the desired location in a body passageway. The urethral (or sleeve) section 34 of the catheter can softly conform to the wall of urethral tract to provide a gentle leak-proof fit. The stylet 104 is then withdrawn from the catheter 5 by grasping the catheter to maintain it in place as the stylet is gently pulled out of the catheter. Alternatively, the stylet 104 can be withdrawn before the balloon portion 24 is expanded. The end piece 80 of the catheter is connected to a connector tube which leads to a bag for holding urine.

To remove the catheter from the body, the shroud 51 can be grasped by hand and gently pulled while the sleeve section 34 of the catheter is firmly held so that the collar 50 with shroud 51 is slipped proximally over the reservoir section 30. If the collar 50 and the shroud 51 are separate, the collar can be similarly removed by pulling. Subsequently, the sleeve portion 26 of the cavity, no longer being restricted by the collar 50, allows the fluid to freely return from the balloon portion 24 to the reservoir portion 22, thus deflating the balloon portion to facilitate the removal of the catheter from the body passa way.

The catheter of the present invention can be made so that the enclosed cylindrical sleeve cavity contains a lubricant. An example of lubricant effective for lubricating the sliding of the overcoat on the surface of inner tube and reduction of friction is petrolatum or liquid soap. The lubricant and the method of incorporating the lubricant into the cavity as disclosed in U.S. Pat. No. 5,098,379 (Conway et al.) are incorporated by reference herein.

The female catheter can also include bactericidal agents. One embodiment is to incorporate the bactericidal agents into the polymeric matrix of at least a portion of the overcoat layer of the cannula or catheter. The polymeric matrix preferably includes cured silicon rubber. The bactericidal agent and the method of incorporating such bactericidal agent into the matrix of the overcoat layer as disclosed in U.S. Pat. No. 5,261,896 (Conway et al.) are incorporated by reference herein. Another method of providing bactericidal effect by the catheter is to incorporate bactericidal agents in the substance, such as a lubricant, contained in the cavity defined by the overcoat layer and the inner tube with a means provided for the diffusion of the bactericidal agents out of the cavity. The bactericidal agents and the method of incorporating these agents into the catheter as disclosed in U.S. Pat. No. 5,269,770 (Conway et al.) are incorporated by reference herein.

Figure 19:
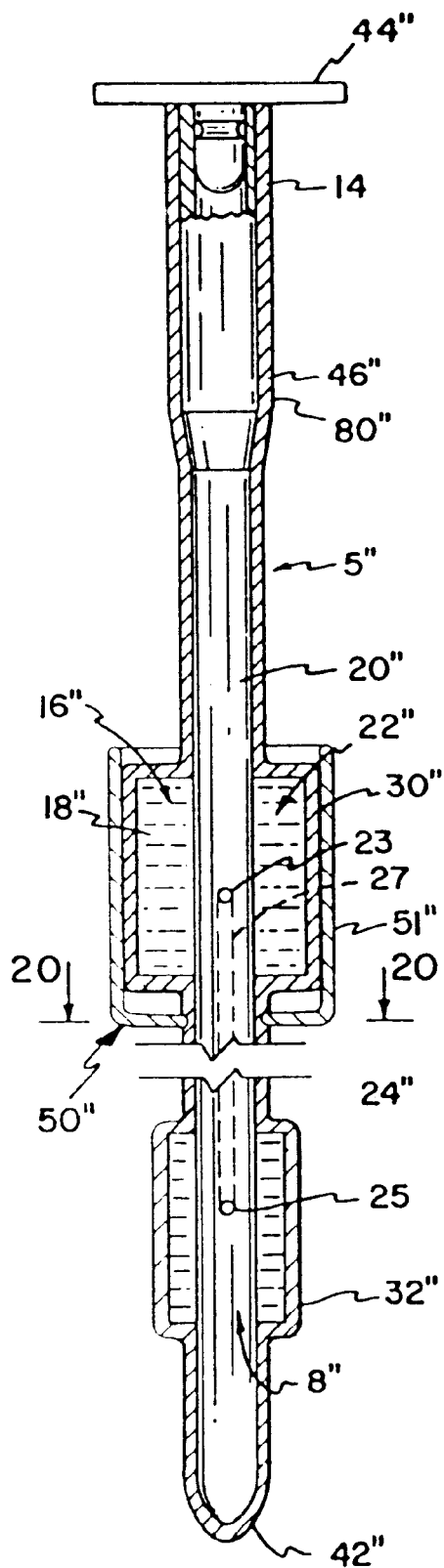
FIG. 19 is a transverse schematic view of another embodiment of an retention catheter in accordance of the present invention, similar to the view of FIG. 1.
Figure 20:
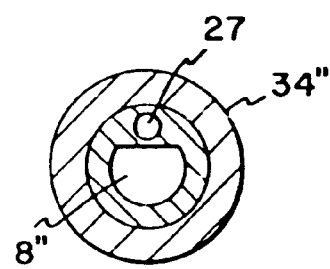
FIG. 20 is a cross-sectional view of the retention catheter shown in FIG. 19 as seen generally from the line 20—20 thereof.

Another embodiment is a catheter (as shown in FIGS. 19–20) having channel 27 in the wall of the inner tube that provides fluid communication between the balloon cavity 24" and the reservoir cavity 22" (the features of the primed numbers in FIGS. 19–20 correspond to the features of corresponding numbers in FIG. 1). The reservoir cavity 22" has a cylindrical narrow portion 26" distal thereto extending toward but not communicating with the reservoir cavity 22'". The channel enters the balloon portion 24" of the cavity at an opening 25 and enters the cylindrical, narrow portion 26" of the reservoir cavity at an opening 23. Such an inner tube can be made by injection molding. Another embodiment is a catheter similar to the retention catheter described hereinabove in FIG. 1 with the differences that the balloon section of the catheter has a much larger geometry (i.e., diameter) than that shown in FIG. 1. If preferred, catheters with more than one cavity wherein the cavity has one or more portions of different diameters can be made with the method of the present invention.

A catheter of the present invention can also be packaged in a vapor barrier pack (such as metal foil or plastic) with a stylet inserted in the catheter to reduce the loss of fluid. Such a package can be sold as a kit commercially.

It is to be understood that even though numerous characteristics and advantages of the present invention have been set forth in the foregoing description, together with details of the structure and function of the invention, the sequence or order of the specific steps, or the actual compositions, solvents, temperatures, environmental conditions and the like employed for each step, it will be appreciated the disclosure is illustrative only, and that changes may be made in detail, especially in matters of shape, size, arrangement of parts or sequence or elements of events within the principles and spirit of the invention. For example, in making a shaped structure with the method of the present invention, the liquid composition for forming the inner piece can be a nonpolymeric material such as a composition containing an inorganic dispersion such as clay or a molten metal such as lead. Likewise, the liquid composition for coating the bond-preventing agent need not be polymeric.

What is claimed is:

1. A method of catheterizing a patient, comprising:

urging a hand-actuated retention catheter into a body passageway from a space exterior thereto, said catheter comprising a tube having outer and inner surfaces, the inner surface defining an inner lumen, an overcoat layer encircling the tube, the overcoat layer having interior and exterior surfaces, a cavity interposed between the tube and the overcoat layer, a fluid within the cavity, and a restriction collar with a shroud; said cavity encircling the tube and being defined by portions of the outer surface of the tube in cooperation with portions of the interior surface of the overcoat layer, wherein the overcoat layer includes an expandable, resilient balloon section, a fluid reservoir section proximal thereto, and a catheter sleeve section interconnecting said balloon section and said reservoir section, each of such sections corresponds to a corresponding section of the catheter; the overcoat layer being joined to the outer surface of the tube at distal and proximal ends of the cavity; the cavity including a balloon portion, a fluid reservoir portion, and a catheter sleeve portion thereof interconnecting said balloon portion and said reservoir portion; wherein the catheter sleeve section of the overcoat layer defines a narrowing in cavity through which fluid passing from the fluid reservoir portion and the balloon portion thereof must pass; the collar being encircling the sleeve section to restrict flow in the sleeve portion of the cavity and the shroud encircling the reservoir section to limit the lateral ballooning thereof;

compressing the shroud-encircled reservoir section to force fluid through the sleeve portion to the balloon portion of the cavity; and subsequently removing the collar with the shroud from the catheter to enable withdrawal of the catheter from the body passageway.

2. The method of claim 1 wherein the step of urging the catheter is a result of pushing a stylet inserted into the lumen of the inner tube.

* * * * *